(12) United States Patent
Weiss et al.

(10) Patent No.: US 7,846,898 B2
(45) Date of Patent: Dec. 7, 2010

(54) PHEROMONES AND THE LUTEINIZING HORMONE FOR INDUCING PROLIFERATION OF NEURAL STEM CELLS AND NEUROGENESIS

(75) Inventors: Samuel Weiss, Calgary (CA); Emeka Enwere, Calgary (CA); Linda Andersen, Calgary (CA); Christopher Gregg, Calgary (CA)

(73) Assignee: Stem Cell Therapeutics Corp.

( * ) Notice: Subject to any disclaimer, the term of this patent is extended or adjusted under 35 U.S.C. 154(b) by 0 days.

(21) Appl. No.: 11/058,441

(22) Filed: Feb. 14, 2005

(65) Prior Publication Data

US 2005/0245436 A1 Nov. 3, 2005

Related U.S. Application Data

(60) Provisional application No. 60/544,915, filed on Feb. 13, 2004.

(51) Int. Cl.
*A61K 38/00* (2006.01)
*C12N 5/0797* (2010.01)
*C12N 5/079* (2010.01)

(52) U.S. Cl. .......................... 514/12; 514/2; 424/198.1; 435/377

(58) Field of Classification Search .................. 435/375
See application file for complete search history.

(56) References Cited

U.S. PATENT DOCUMENTS

| | | | |
|---|---|---|---|
| 4,703,008 A | 10/1987 | Lin | |
| 4,902,680 A | 2/1990 | Aroonsakul | |
| 5,023,252 A | 6/1991 | Hseih | |
| 5,128,242 A | 7/1992 | Arimura et al. | |
| 5,198,542 A | 3/1993 | Onda et al. | |
| 5,208,320 A | 5/1993 | Kitada et al. | |
| 5,268,164 A | 12/1993 | Kozarich et al. | |
| 5,326,860 A | 7/1994 | Onda et al. | |
| 5,441,868 A | 8/1995 | Lin | |
| 5,505,206 A | 4/1996 | Walloch | |
| 5,506,107 A | 4/1996 | Cunningham et al. | |
| 5,506,206 A | 4/1996 | Kozarich et al. | |
| 5,527,527 A | 6/1996 | Friden | |
| 5,547,935 A | 8/1996 | Mullenbach et al. | |
| 5,547,993 A | 8/1996 | Miki | |
| 5,559,143 A | 9/1996 | McDonald et al. | |
| 5,614,184 A | 3/1997 | Sytkowski et al. | |
| 5,621,080 A | 4/1997 | Lin | |
| 5,623,050 A | 4/1997 | Kitada et al. | |
| 5,686,416 A | 11/1997 | Kozarich et al. | |
| 5,723,115 A | 3/1998 | Serrero | |
| 5,750,376 A | 5/1998 | Weiss et al. | |
| 5,753,506 A | 5/1998 | Johe | |
| 5,773,569 A | 6/1998 | Wrighton et al. | |
| 5,801,147 A | 9/1998 | Kitada et al. | |
| 5,833,988 A | 11/1998 | Friden | |
| 5,837,460 A | 11/1998 | Von Feldt et al. | |
| 5,851,832 A | 12/1998 | Weiss et al. | |
| 5,877,169 A | 3/1999 | Simpkins | |
| 5,885,574 A | 3/1999 | Elliott | |
| 5,955,346 A | 9/1999 | Wells et al. | |
| 5,977,307 A | 11/1999 | Friden et al. | |
| 5,980,885 A | 11/1999 | Weiss et al. | |
| 6,015,555 A | 1/2000 | Friden | |
| 6,048,971 A | 4/2000 | Sytkowski et al. | |
| 6,165,783 A | 12/2000 | Weiss et al. | |
| 6,191,106 B1 | 2/2001 | Mullenbach et al. | |
| 6,239,105 B1 | 5/2001 | Brewitt | |
| 6,242,563 B1 | 6/2001 | Dong | |
| 6,294,346 B1 | 9/2001 | Weiss | |
| 6,329,508 B1 | 12/2001 | Friden | |
| 6,333,031 B1 | 12/2001 | Olsson et al. | |
| 6,376,218 B1 | 4/2002 | Hsu et al. | |
| 6,413,952 B1 | 7/2002 | Luengo et al. | |
| 6,429,186 B1 | 8/2002 | Fuh et al. | |
| 6,618,698 B1 | 9/2003 | Beausoleil et al. | |
| 7,048,934 B2 * | 5/2006 | Thompson et al. | 424/198.1 |
| 7,514,072 B1 | 4/2009 | Ehrenreich et al. | |
| 2002/0098178 A1 | 7/2002 | Brand et al. | |
| 2003/0130197 A1 | 7/2003 | Smith-Swintosky et al. | |
| 2003/0144203 A1 | 7/2003 | Bowen | |
| 2004/0209812 A1 | 10/2004 | Renzi et al. | |
| 2005/0009847 A1 | 1/2005 | Bertilsson et al. | |
| 2006/0089309 A1 | 4/2006 | Tucker et al. | |
| 2008/0286234 A1 | 11/2008 | Eyink | |
| 2010/0028361 A1 | 2/2010 | Smith et al. | |
| 2010/0047233 A1 | 2/2010 | Smith et al. | |

FOREIGN PATENT DOCUMENTS

CA 2175992 5/1995

(Continued)

OTHER PUBLICATIONS

Curtis et al, Cell Cycle, 2(5): 428-430, 2003.*

(Continued)

*Primary Examiner*—Gary B. Nickol
*Assistant Examiner*—Daniel C Gamett
(74) *Attorney, Agent, or Firm*—McKeon Meunier Carlin Curfman

(57) ABSTRACT

The present invention provides a method of increasing neural stem cell numbers or neurogenesis by using a pheromone, a luteinizing hormone (LH) and/or a human chorionic gonadotrophin (hCG). The method can be practiced in vivo to obtain more neural stem cells in situ, which can in turn produce more neurons or glial cells to compensate for lost or dysfunctional neural cells. The method can also be practiced in vitro to produce a large number of neural stem cells in culture. The cultured stem cells can be used, for example, for transplantation treatment of patients or animals suffering from or suspected of having neurodegenerative diseases or conditions.

18 Claims, 15 Drawing Sheets

FOREIGN PATENT DOCUMENTS

| CA | 2 353 553 A1 | 6/2000 |
|---|---|---|
| WO | WO 93 01275 | 1/1993 |
| WO | WO 94 10292 | 5/1994 |
| WO | WO 95/13364 | 5/1995 |
| WO | WO9615226 | 5/1996 |
| WO | WO 96/40231 | 12/1996 |
| WO | WO 97/48729 | 12/1997 |
| WO | WO 99 15191 | 4/1999 |
| WO | WO 99 21966 | 5/1999 |
| WO | WO 00 05260 | 2/2000 |
| WO | WO 00 13650 | 3/2000 |
| WO | WO 01 28574 | 4/2001 |
| WO | WO0159074 | 8/2001 |
| WO | WO 02/085311 | 10/2002 |
| WO | WO 03/035475 A1 | 5/2003 |
| WO | WO 03 040310 | 5/2003 |
| WO | WO2004011021 A1 | 2/2004 |
| WO | WO2004011632 A3 | 2/2004 |
| WO | WO2006037233 | 4/2006 |
| WO | WO2006037233 A1 | 4/2006 |
| WO | WO2009057111 | 5/2009 |

OTHER PUBLICATIONS

Arlotta et al, Annals of the New York Academy of Sciences, 991(1): 229-236, 2003.*
Ostenfeld et al, Adv Tech Stand Neurosurg, 28: 3-89, 2003.*
Bithell et al, (Clinical Science, 108: 13-22, 2003.*
Parker et al, (Experimental Neurology, 194: 320-332, 2005.*
Gage (Science, 287: 14331438, 2000.*
Misra et al, J Pharm Pharmaceutic Sci,, 6(2): 252-273, 2003.*
Al-Hader, A.A., et al. (1997). Novel expression of functional luteinizing hormone/chorionic gonadotropin receptors in cultured glial cells from neonatal rat brains. Biology of Reproduction 56:501-507.
Al-Hader, A.A., et al. (1997). Neurons from fetal rat brain contains functions luteinizing hormone/chorionic gonadotropin receptors. Biology of Reproduction 56:1071-1076.
Karbanova, J., et al. (2004). Neural stem cells transplanted into intact brains as neurospheres form solid grafts composed of neurons, astrocytes and oligodendrocyte precursors. Biodmed. Papers 148(2):217-220.
Lei, Z.M., et al. (2001). Neural actions of luteinizing hormone and human chorionic gonadotropin. Seminars in Reproductive Medicine 19(1):103-109.
Reynolds, B.A., and Weiss, S. (1996). Clonal and population analyses demonstrate that an EGF-responsive mammalian embryonic CNS precursor is a stem cell. Developmental Biology 175:1-13.
Brown, J. et al. (2003). Enriched environment and physical activity stimulate hippocampal but not olfactory bulb neurogenesis. Eur J Neurosci. 17(10):2042-2046.
Dulac, C., and Torello, A.T. (2003). Molecular detection of pheromone signals in mammals: from genes to behaviour. Nat Rev Neurosci. 4(7):551-562.
Fernandez-Pol, J.A. (1985). Epidermal growth factor receptor of A431 cells. Characterization of a monoclonal anti-receptor antibody noncompetitive agonist of epidermal growth factor action. J. Biol. Chem. 260(8):5003-5011.
Fowler, C.D., et al. (2002). The effects of social environment on adult neurogenesis in the female prairie vole. J. Neurobiology 51(2):115-128.
Frisén, J., et al. (1998). Central nervous system stem cells in the embryo and adult. Cell Mol Life Sci. 54(9):935-945.
Gage, F.H. (2000). Mammalian neural stem cells. Science 287(5457):1433-1438.
Huhtaniemi, I. et al. (2002). Transgenic and knockout mouse models for the study of luteinizing hormone and luteinizing hormone receptor function. Mol Cell Endocrinol. 187(1-2):49-56.
Johnson, D.L., and Jolliffe, L.K. (2000). Erythropoietin mimetic peptides and the future. Nephrol. Dial. Transplant. 15(9):1274-1277.
Kaushansky, K. (2001). Hematopoietic growth factor mimetics. Ann. N.Y. Acad. Sci. 938:131-138.
Kempermann, G., and Gage, F.H. (1999). Experience-dependent regulation of adult hippocampal neurogenesis: effects of long-term stimulation and stimulus withdrawal. Hippocampus. 9(3):321-332.
Kiyokawa, Y., et al. (2004). Modulatory role of testosterone in alarm pheromone release by male rats. Horm Behav. 45(2):122-127.
Luskin, M.B. (1993). Restricted proliferation and migration of postnatally generated neurons derived from the forebrain subventricular zone. Neuron. 11(1):173-189.
Ma, W., et al. (1998). Role of the adrenal gland and adrenal-mediated chemosignals in suppression of estrus in the house mouse: the lee-boot effect revisited. Biol Reprod. 59(6):1317-1320.
Menezes, J.R., et al. (1995). The division of neuronal progenitor cells during migration in the neonatal mammalian forebrain. Mol Cell Neurosci. 6(6):496-508.
Mode, A., et al. (1996). The human growth hormone (hGH) antagonist $^{G120R}$hGH does not antagonize GH in the rat, but has paradoxical agonist activity, probably via the prolactin receptor. Endocrinology 137(2):447-454.
Moro, O., and Lerner, E.A. (1997). Maxadilan, the vasodilator from sand flies, is a specific pituitary adenylate cyclase activating peptide type I receptor agonist. J. Biol. Chem. 272(2):966-970.
Morrison, S.J., et al. (1997). Regulatory mechanisms in stem cell biology. Cell 88:287-298.
Morshead, C.M., and van der Kooy, D. (1992). Postmitotic death is the fate of constitutively proliferating cells in the subependymal layer of the adult mouse brain. J Neurosci. 12(1):249-256.
Nilsson, M., et al. (1999). Enriched environment increased neurogenesis in the adult rat dentate gyrus and improves spatial memory. J Neurobiol. 39(4):569-578.
Peretto, P., et al. (1999). The subependymal layer in rodents: a site of structural plasticity and cell migration in the adult mammalian brain. Brain Res Bull. 49(4):221-243.
Rao, M.S. (1999). Multipotent and restricted precursors in the central nervous system. Anat Rec. 257(4):137-148.
Reynolds, B.A., and Weiss, S. (1992). Generation of neurons and astrocytes from isolated cells of the adult mammalian central nervous system. Science 255(5052):1707-1710.
Reynolds, J.N., et al. (1992). Ethanol modulation of GABA receptor-activated Cl$^-$ currents in neurons of the chick, rat and mouse central nervous system. Eur J Pharmacol. 224(2-3):173-181.
Rochefort, C., et al. (2002). Enriched odor exposure increases the number of newborn neurons in the adult olfactory bulb and improves odor memory. J Neurosci. 22(7):2679-2689.
Rodriguez-Peña, A. (1999). Oligodendrocyte development and thyroid hormone. J Neurobiol. 40(4):497-512.
Shingo, T., et al. (2003). Pregnancy-stimulated neurogenesis in the adult female forebrain mediated by prolactin. Science 299(5603):117-120.
Tanapat, P., et al. (1999). Estrogen stimulates a transient increase in the number of new neurons in the dentate gyrus of the adult female rat. J Neurosci. 19(14):5792-5801.
Weiss, S., et al. (1996). Is there a neural stem cell in the mammalian forebrain? Trends Neuroscience 19:387-393.
Wrighton, N.C., et al. (1996). Small peptides as potent mimetics of the protein hormone erythropoietin. Science 273(5274):458-463.
Zhang, F.P. et al. (2001). Normal prenatal but arrested postnatal sexual development of luteinizing hormone receptor knockout (LuRKO) mice. Mol Endocrinol. 15(1):172-183.
Zhang, J.X., et al.. (2001). Scent, social status, and reproductive condition in rat-like hamsters (*Cricetulus triton*). Physiol Behav. 74(4-5):415-420.
U.S. Appl. No. 11/687,302, filed Mar. 16, 2007, Weiss et al.
Al-Hader et al., "Fetal rat brains contain luteinizing hormone/human chorionic gonadotropin receptors," Early Pregnancy: Biol. and Med. 3:323-329 (1997).
Ehrenreich et al., "Erythropoietin Therapy for Acute Stroke Is Both Safe and Beneficial," Mol. Med. 8(8):495-505 (2002).
Lei et al., "Novel Expression of Human Chorionic Gonadotropin/Luteinizing Hormone Receptor Gene in Brain," Endocrinol. 132(5):2262-2270 (1993).
Rao et al., "Human chorionic gonadotropin/luteinizing hormone receptor expression in the adult rat spinal cord," J. Neurosci. Letters 336:135-138 (2003).

Trinchard-Lugan et al., "Pharmacokinetics and pharmacodynamics of recombinant human chorionic gonadotrophin in healthy male and female volunteers," Reproductive BioMed. Online; www.rbmonline.com/Article/280, Jan. 8, 2002.

Belayev et al. "A Novel Neurotrophic Therapeutic Strategy for Experimental Stroke." Brain Research. 1280, 117-123 (2009).

English translation of RU 2003339 C1. Russian Federation Committee for Patents and Trademarks. Published Nov. 30, 1993.

Torner et al. "Prolactin Prevents Chronic Stress-Induced Decrease of Adult Hippocampal Neurogenesis and Promotes Neuronal Fate." *The Journal of Neuroscience*. 29(6): 1826-1833. Feb. 11, 2009.

Webber et al. "Gonadotropins and Alzheimer's Disease: the Link Between Estrogen Replacement Therapy and Neuroprotection."*Acta Neurobiol Exp*. 2004, 64: 113-118.

Barron, A. et al. "Time- and Dose-Dependent Effects of Ovariectomy and Human Chorionic Gonadotropin Treatment on Beta Amyloid and Isoprostane Levels in the PS1M146V Mouse Model of Alzheimer's Disease." P1-436. ICAD Jul./Aug. 2008.

Belayev, L. et al. "Neuroprotective Effect of Human Chorionic Gonadotropin in Transient Focal Cerebral Ischemia in Rats," Poster. International Stroke Conference. San Antonio, TX, Feb. 23-26, 2010.

Belayev, L. et al. "A novel neurotrophic therapeutic strategy for experimental stroke." Brain Research 1280 pp. 117-123 (2009).

Choi, H.K. and Waxman, D. "Growth Hormone, but Not Prolactin, Maintains Low-Level Activation of STAT5a and STAT5b in Female Rat Liver." Endocrinology 140: 5126-5135, 1999.

Chojnacki, A. and Weiss, S., "Expression and putative function of MASH1 and MASH2 in EGF-responsive forebrain neural stem cells." Society for Neuroscience, Presentation No. 600.14. Nov. 8, 2000. (abstract).

Cramer, S. et al. "The Beta-hCG + Erythropoietin in Acute Stroke (BETAS) Study. A 3-Center, Single Dose, Open-Label, Noncontrolled, Phase IIa Safety Trial," Stroke. pp. 1-4. Published online Mar. 4, 2010.

Curtis, M. et al. "Neurogenesis in the Diseased Adult Human Brain," Cell Cycle 2:5, 428-430; Sep./Oct. 2003.

Davidoff, A.W. et al., "Open labeled, uncontrolled pharmacokinetic study of a single intramuscular hCG dose in healthy male volunteers." International Journal of Clinical Pharmacology and Therapeutics, vol. 47: 1-9, Jul. 5, 2009.

Eriksson, P. et al., "Neurogenesis in the adult human hippocampus," Nature Medicine, vol. 4, No. 11: 1313-1317. Nov. 1998.

Faden, A. et al. "Treatment of experimental stroke: Comparison of naloxone and thyrotropin releasing hormone." Neurology; 32: 1083-7. 1982.

Garber, Ken. "Stroke treatment—light at the end of the tunnel?" Nature Biotechnology vol. 25, No. 8, Aug. 2007.

Kolb, B. et al. "Growth factor-stimulated generation of new cortical tissue and functional recovery after stroke damage to the motor cortex of rats." Journal of Cerebral Blood Flow & Metabolism. pp. 1-15, 2006.

Le Cotonnec, J.Y. et al., "Clinical pharmacology of recombinant human luteinizing hormone: Part II. Bioavailability of recombinant human luteinizing hormone assessed with an immunoassay and an in vitro bioassay," Fertility and Sterility vol. 69, No. 2 Feb. 1998.

Mannaerts, B.M.J.L. et al., "A randomized three-way cross-over study in healthy pituitary-suppressed women to compare the bioavailability of human chorionic gonadotrophin (Pregnyl) after intramuscular and subcutaneous administration," Human Reproduction vol. 13 No. 6 pp. 1461-1464, 1998.

Markianos, M. et al. "Serum and Cerebrospinal Fluid Prolactin levels in Male and Female Patients with Clinically-Isolated Syndrome or Relapsing-Remitting Multiple Sclerosis." Journal of Neuroendrocrinology 2010; 22: 503-508.

Sato, A. et al., "Cystine Knot of the Gonadotropin α Subunit Is Critical for Intracellular Behavior but Not for in Vitro Biological Activity," The Journal of Biological Chemistry. vol. 272, No. 29, Issue of Jul. 18, pp. 18098-18103, 1997.

Wehmann, R. and Nisula, B. "Metabolic and Renal Clearance Rates of Purified Human Chorionic Gonadotropin." J. Clin. Invest. copyright The American Society for Clinical Investigation Inc. 0021-9738/81/07/0184/11 vol. 68, pp. 184-194. Jul. 1981.

XP-002582723, NCT00362414 on Aug. 9, 2006: ClinicalTrials.gov Archive.

Woody et al., "Prolactin exerts hematopoietic growth-promoting effects in vivo and partially counteracts myelosuppression by azidothymidine," Experimental Hematology 27: 811-816. 1999.

Minnerup et al., "The Efficacy of Erythropoietin and Its Analogues in Animal Stroke Models: A Meta Analysis," American Heart Association, Inc. pp. 3113-3120. 2009.

Ehrenreich et al., "Recombinant Human Erythropoietin in the Treatment of Acute Ischemic Stroke," Stroke. 2009; 40:00-00.

Bayer, S.A., "Neuron Production in the Hippocampus and Olfactory Bulb of the Adult Rat Brain: Addition or Replacement?," Ann N Y Acad Sci., vol. 457, pp. 163-172, 1985.

Bernichtein, S., et al., "S179D-human PRL, a pseudophosphorylated human PRL analog, is an agonist and not an antagonist," Endocrinology, vol. 142, No. 9, pp. 3950-3963, 2001.

Cerami, A. et al., "Effects of Epoetin Alfa on the Central Nervous System," Seminars in Oncology, vol. 28, No. 2. Suppl 8, pp. 66-70, 2001.

Craig, C.G., et al., "In Vivo Growth Factor Expansion of Endogenous Subependymal Neural Precursor Cell Populations in the Adult Mouse Brain," J Neurosci., vol. 16, No. 8, pp. 2649-2658, 1996.

Dicicco-Bloom et al., "The PACAP Ligand/Receptor System Regulates Cerebral Cortical Neurogenesis," Ann. N.Y. Acad. Sci., vol. 865, pp. 274-289, 1998.

Freed, C.R., et al., "Survival of Implanted Fetal Dopamine Cells and Neurologic Improvement 12 to 46 Months After Transplantation for Parkinson's Disease," N Engl J Med., vol. 327, No. 22, pp. 1549-1555, 1992.

Kaplan, M.S., "Neurogenesis in the 3-month-old Rat Visual Cortex," J Comp Neurol. vol. 195, No. 2, pp. 323-338, 1981.

Park, K.I., "Transplantation of Neural Stem Cells: Cellular & Gene Therapy for Hypoxic-Ischemic Brain Injury,"Yonsei Med. J., vol. 41, No. 6, pp. 825-835, 2000.

Patil, A-A., "The Effect of Human Chorionic Gonadotropin (HCG) on Restoration of Physiological Continuity of the Spinal Cord. A Preliminary Report," Int. Surg., vol. 75, pp. 54-57, 1990.

Patil, A-A., "The Study of the Effect of Human Chorionic Gonadotrophic (HCG) Hormone on the Survival of Adrenal Medulla Transport in Brain. Preliminary Study," Acta Neurochirurgica, vol. 87, pp. 76-78, 1987.

Patil, A-A. and Nagaraj, M.P., "The Effect of Human Chorionic Gonadotropin (HCG) on Functional Recovery of Spinal Cord Sectioned Rats," Acta Neurochirurgica, vol. 69, pp. 205-218, 1983.

Patil, A-A. And Nagaraj, M.P., Neurosurgery, vol. 12, No. 5, pp. 593-594, 1983.

Perlow, M.J., et al., "Brain grafts reduce motor abnormalities produced by destruction of nigrostriatal dopamine system," Science, vol. 204, No. 4393, pp. 643-647, 1979.

Potten, C.S. And Loeffler, M., "Stem cells: attributes, cycles, spirals, pitfalls and uncertainties Lessons for and from the crypt," Development, vol. 110, No. 4, pp. 1001-1020, 1990.

Rakic, P., "Limits of neurogenesis in primates," Science, vol. 227, No. 4690, pp. 1054-1056, 1985.

Rietze, R., et al., "Mitotically active cells that generate neurons and astrocytes are present in multiple regions of the adult mouse hippocampus," J Comp Neurol., vol. 424, No. 3, pp. 397-408, 2000.

Shingo, T., et al., "Erythropoietin regulates the in vitro and in vivo production of neuronal progenitors by mammalian forebrain neural stem cells," J Neurosci., vol. 21, No. 24, pp. 9733-9743, 2001.

Spencer, D.D., et al., "Unilateral transplantation of human fetal mesencephalic tissue into the caudate nucleus of patients with Parkinson's disease," N Engl J Med., vol. 327, No. 22, pp. 1541-1548, 1992.

Van Der Kooy, D. and Weiss, S., "Why stem cells?," Science, vol. 287, vol. 5457, pp. 1439-1441, 2000.

Widner, H., et al., "Bilateral fetal mesencephalic grafting in two patients with Parkinsonism induced by 1-methyl-4-phenyl-1,2,3,6-tetrahydropyridine (MPTP)," N Engl J Med., vol. 327, No. 22, pp. 1556-1563, 1992.

* cited by examiner

| 2D F-M | 2D F-F | 7D F-M | 7D F-F | 14D F-M | 14D F-F |
|---|---|---|---|---|---|
| 2017 | 2087 | 2978 | 2129 | 1327 | 2062 |
| 1975 | 1943 | 2962 | 2261 | 1422 | 2100 |
| 1972 | 2273 | | 2197 | 1243 | 2208 |

| | 2D F-M | 2D F-F | 7D F-M | 7D F-F | 14D F-M | 14D F-F |
|---|---|---|---|---|---|---|
| | 1988 | 2101 | 2970 | 2195.667 | 1330.667 | 2123.333 |
| | 25.15949 | 165.4449 | 11.31371 | 66.0101 | 89.55631 | 75.74519 |
| | 14.52584 | 95.51963 | 8 | 38.11095 | 51.70536 | 43.7315 |

| 2D M-F | 2D M-M | 7D M-F | 7D M-M | 14D M-F | 14D M-M |
|---|---|---|---|---|---|
| 2398 | 1931 | 1950 | 1862 | 1886 | 1958 |
| 2349 | 1842 | 1900 | 1897 | 1899 | 1896 |
| 2170 | 1910 | 1904 | 1850 | 1809 | 1842 |

| 2D M-F | 2D M-M | 7D M-F | 7D M-M | 14D M-F | 14D M-M |
|---|---|---|---|---|---|
| 2305.667 | 1894.333 | 1918 | 1869.667 | 1864.667 | 1898.667 |
| 120.0181 | 46.5224 | 27.78489 | 24.41994 | 48.64497 | 58.04596 |
| 69.29246 | 26.85972 | 16.04161 | 14.09886 | 28.08519 | 33.51285 | t-Test: Two-Sample Assuming Unequal Variances

|  | Variable 1 | Variable 2 |
|---|---|---|
| Mean | 2305.667 | 1894.333 |
| Variance | 14404.33 | 2164.333 |
| Observatio | 3 | 3 |
| Hypothesiz | 0 | |
| df | 3 | |
| t Stat | 5.534912 | |
| P(T<=t) on | 0.005812 | |
| t Critical or | 2.353363 | |
| P(T<=t) tw | 0.011623 | |
| t Critical tw | 3.182449 | |

| 2D F-M | 2D F-F | 7D F-M | 7D F-F | 14D F-M | 14D F-F |
|---|---|---|---|---|---|
| 108 | 146 | 150 | 94 | 197 | 334 |
| 134 | 112 | 181 | 140 | 228 | 390 |
| 107 | 152 | 189 | 120 | 206 | 480 |

| 2D F-M | 2D F-F | 7D F-M | 7D F-F | 14D F-M | 14D F-F |
|---|---|---|---|---|---|
| 116.3333 | 136.6667 | 173.3333 | 118 | 210.3333 | 401.3333 |
| 15.30795 | 21.57159 | 20.59935 | 23.06513 | 15.94783 | 73.65686 |
| 8.838049 | 12.45436 | 11.89304 | 13.31666 | 9.207485 | 42.52581 |

| 2D M-F | 2D M-M | 7D M-F | 7D M-M | 14D M-F | 14D M-M |
|---|---|---|---|---|---|
| 1293 | 737 | 890 | 790 | 782 | 738 |
| 1270 | 800 | 812 | 838 | 828 | 876 |
| 1099 | 734 | 778 | 700 | 830 | 720 |

| 2D M-F | 2D M-M | 7D M-F | 7D M-M | 14D M-F | 14D M-M |
|---|---|---|---|---|---|
| 1220.667 | 757 | 826.6667 | 776 | 813.3333 | 778 |
| 105.9921 | 37.26929 | 57.42241 | 70.05712 | 27.15388 | 85.34635 |
| 61.19459 | 21.51743 | 33.15284 | 40.4475 | 15.6773 | 49.27474 | t-Test: Two-Sample Assuming Unequal Variances

|  | Variable 1 | Variable 2 |
|---|---|---|
| Mean | 1220.667 | 757 |
| Variance | 11234.33 | 1389 |
| Observatioı | 3 | 3 |
| Hypothesiz | 0 | |
| df | 2 | |
| t Stat | 7.147917 | |
| P(T<=t) onɛ | 0.009508 | |
| t Critical on | 2.919987 | |
| P(T<=t) twc | 0.019016 | |
| t Critical twɩ | 4.302656 | |

A. TUNEL 7-day females SVZ

B. TUNEL OB-chase females

2-Day Female ICV SVZ

| LH | VEH |
|---|---|
| 3239 | 1999 |
| 3174 | 2089 |
| 3045 | 2087 |
| 2972 | 2203 |

| LH | VEH |
|---|---|
| 3107.5 | 2094.5 |
| 121.079863 | 83.6241592 |
| 60.5399317 | 41.8120796 | t-Test: Two-Sample Assuming Unequal Variances

|  | Variable 1 | Variable 2 |
|---|---|---|
| Mean | 3107.5 | 2094.5 |
| Variance | 14660.3333 | 6993 |
| Observations | 4 | 4 |
| Hypothesized | 0 | |
| df | 5 | |
| t Stat | 13.7681966 | |
| P(T<=t) one- | 1.8141E-05 | |
| t Critical one- | 2.01504918 | |
| P(T<=t) two- | 3.6281E-05 | |
| t Critical two- | 2.57057764 | |

6-Day LH/VEH female ICV SVZ

| LH | VEH |
|---|---|
| 3612 | 2458 |
| 3150 | 2150 |
| 3033 | 2299 |
| 2805 | 2332 |

| LH | VEH |
|---|---|
| 3150 | 2309.75 |
| 339.6851483 | 126.634316 |
| 169.8425742 | 63.31715802 | t-Test: Two-Sample Assuming Unequal Variances

|  | Variable 1 | Variable 2 |
|---|---|---|
| Mean | 3150 | 2309.75 |
| Variance | 115386 | 16036.25 |
| Observations | 4 | 4 |
| Hypothesized N | 0 | |
| df | 4 | |
| t Stat | 4.635579864 | |
| P(T<=t) one-tai | 0.004883141 | |
| t Critical one-ta | 2.131846486 | |
| P(T<=t) two-tai | 0.009766282 | |
| t Critical two-ta | 2.776450856 | |

2-day males VEH/LH ICV

| LH | VEH |
|---|---|
| 3335 | 2073 |
| 2594 | 1997 |
| 2845 | |

| LH | VEH |
|---|---|
| 2924.667 | 2035 |
| 376.8691 | 53.74012 |
| 217.5855 | 38 | t-Test: Two-Sample Assuming Unequal Variances

| | Variable 1 | Variable 2 |
|---|---|---|
| Mean | 2924.667 | 2035 |
| Variance | 142030.3 | 2888 |
| Observatio | 3 | 2 |
| Hypothesiz | 0 | |
| df | 2 | |
| t Stat | 4.02785 | |
| P(T<=t) on | 0.028234 | |
| t Critical or | 2.919987 | |
| P(T<=t) tw | 0.056468 | |
| t Critical tw | 4.302656 | |

SVZ of Female Mice

Hippocampus of Female Mice

ID CELLS
AND NEUROGENESIS

PHEROMONES AND THE LUTEINIZING HORMONE FOR INDUCING PROLIFERATION OF NEURAL STEM CELLS AND NEUROGENESIS

RELATED APPLICATION

This application claims the benefit of U.S. Provisional Application Ser. No. 60/544,915, filed Feb. 13, 2004, under 35 U.S.C. §119(e). The entire disclosure of the prior application is hereby incorporated by reference.

TECHNICAL FIELD

This invention relates to methods of increasing neural stem cell numbers and neurogenesis, as well as compositions useful therefore.

REFERENCES

U.S. Patent Application Publication No. 20020098178A1.
U.S. Pat. No. 5,023,252.
U.S. Pat. No. 5,128,242.
U.S. Pat. No. 5,198,542.
U.S. Pat. No. 5,208,320.
U.S. Pat. No. 5,268,164.
U.S. Pat. No. 5,326,860.
U.S. Pat. No. 5,506,107.
U.S. Pat. No. 5,506,206.
U.S. Pat. No. 5,527,527.
U.S. Pat. No. 5,547,935.
U.S. Pat. No. 5,614,184.
U.S. Pat. No. 5,623,050.
U.S. Pat. No. 5,686,416.
U.S. Pat. No. 5,723,115.
U.S. Pat. No. 5,750,376.
U.S. Pat. No. 5,773,569.
U.S. Pat. No. 5,801,147.
U.S. Pat. No. 5,833,988.
U.S. Pat. No. 5,837,460.
U.S. Pat. No. 5,851,832.
U.S. Pat. No. 5,885,574.
U.S. Pat. No. 5,977,307.
U.S. Pat. No. 5,980,885.
U.S. Pat. No. 6,015,555.
U.S. Pat. No. 6,048,971.
U.S. Pat. No. 6,191,106.
U.S. Pat. No. 6,242,563.
U.S. Pat. No. 6,329,508.
U.S. Pat. No. 6,333,031.
U.S. Pat. No. 6,413,952.
WO 96/40231.
WO 97/48729.
Brown, J. et al. (2003). Enriched environment and physical activity stimulate hippocampal but not olfactory bulb neurogenesis. Eur J. Neurosci. 17(10):2042-6.
Dulac, C. and Torello, A. T. (2003). Molecular detection of pheromone signals in mammals: from genes to behaviour. Nature Reviews 4:551-562.
Fernandez-Pol, J. A. (1985). Epidermal growth factor receptor of A431 cells. Characterization of a monoclonal antireceptor antibody noncompetitive agonist of epidermal growth factor action. J. Biol. Chem. 260(8):5003-5011.
Fowler, C. D., et al. (2002). The effects of social environment on adult neurogenesis in the female prairie vole. J. Neurobiology 51(2):115-128.
Frisen J., et al. (1998). Central nervous system stem cells in the embryo and adult. Cell Mol Life Sci. 54(9):935-45.
Gage, F. H. (2000). Mammalian neural stem cells. Science 287:1433-1438.
Huhtaniemi, I. et al. (2002). Transgenic and knockout mouse models for the study of luteinizing hormone and luteinizing hormone receptor function. Molecular and Cellular Endocrinology 187: 49-56.
Johnson, D. L. et al. (2000). Erythropoietin mimetic peptides and the future. Nephrol. Dial. Transplant. 15(9):1274-1277.
Kaushansky, K. (2001). Hematopoietic growth factor mimetics. Ann. N.Y. Acad. Sci. 938:131-138.
Kempermann, G. and Gage, F. H. (1999). Experience-dependent regulation of adult hippocampal neurogenesis: effects of long-term stimulation and stimulus withdrawal. Hippocampus. 9(3):321-32.
Kiyokawa, Y. et al. (2004). Modulatory role of testosterone in alarm pheromone release by male rats. Hormones and Behavior 45: 122-127.
Luskin M. B. (1993). Restricted proliferation and migration of postnatally generated neurons derived from the forebrain subventricular zone. Neuron. 11(1): 173-89.
Ma, W. et al. (1998). Role of the Adrenal Gland and Adrenal-Mediated Chemosignals in Suppression of Estrus in the House Mouse: The Lee-Boot Effect Revisited. Biology of Reproduction 59: 1317-1320.
Menezes, J. R. L., et al. (1995). The division of neuronal progenitor cells during migration in the neonatal mammalian forebrain. Molecular and Cellular Neuroscience 6:496-508.
Mode, A., et al. (1996). The human growth hormone (hGH) antagonist G120RhGH does not antagonize GH in the rat, but has paradoxical agonist activity, probably via the prolactin receptor. Endocrinology 137(2):447-454.
Moro, O., et al. (1997). Maxadilan, the vasodilator from sand flies, is a specific pituitary adenylate cyclase activating peptide type I receptor agonist. J. Biol. Chem. 272(2):966-70.
Morrison, S. J., et al. (1997). Regulatory mechanisms in stem cell biology. Cell 88:287-298.
Morshead, C. M. and van der Kooy, D. (1992). Postmitotic death is the fate of constitutively proliferating cells in the subependymal layer of the adult mouse brain. Neurosci. 2(1):249-56.
Nilsson, M., et al. (1999). Enriched environment increased neurogenesis in the adult rat dentate gyrus and improves spatial memory. Journal of Neurobiology 39(4):569-578.
Peretto, P., et al. (1999). The subependymal layer in rodents: A site of structural plasticity and cell migration in the adult mammalian brain. Brain Research Bulletin 49(4):221-243.
Rao, M. S. (1999). Multipotent and restricted precursors in the central nervous system. The Anatomical Record (New Anat.) 257:137-148.
Remington's Pharmaceutical Sciences, Mace Publishing Company, Philadelphia, Pa. 17th Edition (1985).
Reynolds, B. A. and Weiss, S. (1992). Generation of neurons and astrocytes from isolated cells of the adult mammalian central nervous system. Science. 255(5052):1707-10.
Reynolds, J. N., et al. (1992). Ethanol modulation of GABA receptor-activated Cl-currents in neurons of the chick, rat and mouse central nervous system. Eur J. Pharmacol. 224 (2-3):173-81.
Rochefort, C., et al. (2002). Enriched odor exposure increases the number of newborn neurons in the adult olfactory bulb and improves odor memory. The Journal of Neuroscience 22(7):2679-2689.

Rodriguez-Pena A. (1999). Oligodendrocyte development and thyroid hormone. J Neurobiol. 40(4):497-512.

Shingo, T., et al. (2003). Pregnancy-stimulated neurogenesis in the adult female forebrain mediated by prolactin. Science 299:117-120.

Tanapat P, et al. (1999). Estrogen stimulates a transient increase in the number of new neurons in the dentate gyrus of the adult female rat. J. Neurosci. 19(14):5792-801.

Weiss, S., et al. (1996). Is there a neural stem cell in the mammalian forebrain? Trends Neuroscience 19:387-393.

Wrighton, N. C., et al. (1996). Small peptides as potent mimetics of the protein hormone erythropoietin. Science 273(5274):458-464.

Zhang, F. P. et al. (2001). Normal prenatal but arrested postnatal sexual development of luteinizing hormone receptor knockout (LuRKO) mice. Mol Endocrinol. 15(1): 172-83.

Zhang, J. et al. (2001). Scent, social status, and reproductive condition in rat-like hamsters (Cricetulus triton). Physiology & Behavior 74: 415-420.

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

In recent years, neurodegenerative disease has become an important concern due to the expanding elderly population which is at greatest risk for these disorders. Neurodegenerative diseases include the diseases which have been linked to the degeneration of neural cells in particular locations of the central nervous system (CNS), leading to the inability of these cells to carry out their intended function. These diseases include Alzheimer's Disease, Huntington's Disease, Amyotrophic Lateral Sclerosis, and Parkinson's Disease. In addition, probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis. Moreover, brain injuries often result in the loss of neural cells, the inappropriate functioning of the affected brain region, and subsequent behavior abnormalities.

Consequently, it is desirable to supply neural cells to the brain to compensate for degenerate or lost neurons in order to treat neurodegenerative diseases or conditions. One approach to this end is to transplant neural cells into the brain of the patient. This approach requires a source of large amounts of neural cells, preferably from the same individual or a closely related individual such that host-versus-graft or graft-versus-host rejections can be minimized. As it is not practical to remove a large amount of neurons or glial cells from one person to transplant to another, a method to culture large quantity of neural cells is necessary for the success of this approach.

Another approach is to induce the production of neural cells in situ to compensate for the lost or degenerate cells. This approach requires extensive knowledge about whether it is possible to produce neural cells in brains, particularly adult brains, and how.

The development of techniques for the isolation and in vitro culture of multipotent neural stem cells (for example, see U.S. Pat. Nos. 5,750,376; 5,980,885; 5,851,832) significantly increased the outlook for both approaches. It was discovered that fetal brains can be used to isolate and culture multipotent neural stem cells in vitro. Moreover, in contrast to the long time belief that adult brain cells are not capable of replicating or regenerating brain cells, it was found that neural stem cells may also be isolated from brains of adult mammals. These stem cells, either from fetal or adult brains, are capable of self-replicating. The progeny cells can again proliferate or differentiate into any cell in the neural cell lineage, including neurons, astrocytes and oligodendrocytes. Therefore, these findings not only provide a source of neural cells which can be used in transplantations, but also demonstrate the presence of multipotent neural stem cells in adult brain and the possibility of producing neurons or glial cells from these stem cells in situ.

It is therefore desirable to develop methods of efficiently producing neural stem cells for two purposes: to obtain more stem cells and hence neural cells which can be used in transplantation therapies, and to identify methods which can be used to produce more stem cells in situ.

SUMMARY OF THE INVENTION

The present invention provides a method of increasing neural stem cell numbers by using a pheromone, a luteinizing hormone (LH) or human chorionic gonadotrophin (hCG). The method can be practiced in vivo to obtain more neural stem cells in situ, which can in turn produce more neurons or glial cells to compensate for lost or dysfunctional neural cells. The method can also be practiced in vitro to produce a large number of neural stem cells in culture. The cultured stem cells can be used, for example, for transplantation treatment of patients or animals suffering from or suspected of having neurodegenerative diseases or conditions.

Accordingly, one aspect of the present invention provides a method of increasing neural stem cell number, comprising providing an effective amount of a pheromone, an LH or hCG to at least one neural stem cell under conditions which result in an increase in the number of neural stem cells. The neural stem cell may be located in the brain of a mammal, in particular in the subventricular zone of the brain of the mammal. Alternatively, the neural stem cell may be located in the hippocampus of the mammal. Although mammals of all ages can be subjected to this method, it is preferable that the mammal is not an embryo. More preferably, the mammal is an adult.

The mammal may suffer from or be suspected of having a neurodegenerative disease or condition. The disease or condition may be a spinal cord injury or brain injury, such as stroke or an injury caused by a surgery. The disease or condition may be aging, which is associated with a significant reduction in the number of neural stem cells. The disease or condition can also be a neurodegenerative disease, particularly Alzheimer's disease, Huntington's disease, amyotrophic lateral sclerosis, or Parkinson's disease.

Alternatively, the neural stem cell may be in a culture in vitro. When practiced in vitro, it is preferable that LH or hCG is used instead of pheromones.

The pheromone can be any pheromone that is capable of increasing neural stem cell numbers in the mammal. Assays for determining if a substance is capable of increasing neural stem cell numbers are established in the art and described herein (e.g., see Examples 1 and 3). The pheromone is preferably selected from the group consisting of 2-sec-butyl-4,5-dihydrothiazole (SBT), 2,3-dehydro-exo-brevicomin (DHB), alpha and beta farnesenes, 6-hydroxy-6-methyl-3-heptanone, 2-heptanone, trans-5-hepten-2-one, trans-4-hepten-2-one, n-pentyl acetate, cis-2-penten-1-yl-acetate, 2,5-dimethylpyrazine, dodecyl propionate, and (Z)-7-dodecen-1-yl acetate.

Whether the pheromone, LH or hCG is used in vivo or in vitro, other agents may be applied in combination, such as follicle-stimulating hormone (FSH), gonadotropin releasing hormone (GnRH), prolactin, prolactin releasing peptide (PRP) erythropoietin, cyclic AMP, pituitary adenylate cyclase activating polypeptide (PACAP), serotonin, bone morphogenic protein (BMP), epidermal growth factor (EGF), transforming growth factor alpha (TGFalpha), transforming growth factor beta (TGFbeta), fibroblast growth factor (FGF), estrogen, growth hormone, growth hormone releasing hormone, insulin-like growth factors, leukemia inhibitory factor, ciliary neurotrophic factor (CNTF), brain derived neurotrophic factor (BDNF), thyroid hormone, thyroid stimulating hormone, sonic hedgehog (SHH), and/or platelet derived growth factor (PDGF). The LH or hCG may be any LH or hCG analog or variant which has the activity of the native LH or hCG.

Another aspect of the present invention provides a method of treating or ameliorating a neurodegenerative disease or condition in a mammal, comprising providing an effective amount of a pheromone, LH or hCG to the brain of the mammal. The disease or condition may be a CNS injury, such as stroke or an injury caused by a brain/spinal cord surgery. The disease or condition may be aging, which is associated with a significant reduction in the number of neural stem cells. The disease or condition can also be a neurodegenerative disease, particularly Alzheimer's disease, Huntington's disease, amyotrophic lateral sclerosis, or Parkinson's disease.

The mammal can optionally receive a transplantation of neural stem cells and/or neural stem cell progeny. The transplantation may take place before, after, or at the same time the mammal receives the pheromone, LH or hCG. Preferably, the mammal receives the transplantation prior to or concurrently with the pheromone, LH or hCG.

The mammal can optionally receive at least one additional agent, such as erythropoietin, cyclic AMP, pituitary adenylate cyclase activating polypeptide (PACAP), serotonin, bone morphogenic protein (BMP), epidermal growth factor (EGF), transforming growth factor alpha (TGF.alpha.), fibroblast growth factor (FGF), estrogen, growth hormone, insulin-like growth factor 1, and/or ciliary neurotrophic factor (CNTF).

The pheromone, LH/hCG and/or the additional agent can be provided by any method established in the art. For example, they can be administered intravascularly, intrathecally, intravenously, intramuscularly, subcutaneously, intraperitoneally, topically, orally, rectally, vaginally, nasally, by inhalation or into the brain. The administration is preferably performed systemically, particularly by subcutaneous administration. The pheromone, LH/hCG or additional agent can also be provided by administering to the mammal an effective amount of an agent that can increase the amount of endogenous pheromone, LH/hCG or the additional agent in the mammal. For example, the level of LH in an animal can be increased by using GnRH.

When the pheromone, LH/hCG or the additional agent is not directly delivered into the brain, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine-thienylalanine-serine-proline-4-Me-tyrosine.psi.(—$CH_2NH$)-arginine-COOH). Alternatively, the molecules to be delivered can be conjugated to the transferrin receptor antibodies as described in U.S. Pat. Nos. 6,329,508; 6,015,555; 5,833,988 or 5,527,527. The molecules can also be delivered as a fusion protein comprising the molecule and a ligand that is reactive with a brain capillary endothelial cell receptor, such as the transferrin receptor (see, e.g., U.S. Pat. No. 5,977,307).

Another aspect of the present invention provides a method of enhancing neuron formation from neural stem cells, comprising providing a pheromone, LH or hCG to at least one neural stem cell under conditions that result in enhanced neuron formation from said neural stem cell. Further provided is a method of increasing new neuron formation in the olfactory bulb of a mammal, comprising providing an effective amount of a pheromone, LH or hCG to the mammal. Compositions and pharmaceutical compositions comprising a pheromone, LH or hCG, and at least one additional agent are also provided.

Also provided are cellular compositions prepared according to the present invention. In particular, neural stem cell cultures that have been exposed to LH/hCG are provided. These cultures have higher levels of neural stem cells and/or neurons, and can be used, for example, for transplantation.

(A) shows the effects on the number of BrdU positive cells in the SVZ.

(B) shows the effects on the number of Ki67 positive cells in the SVZ.

(C) shows the comparison of littermates and non-littermates.

Figure 2A:
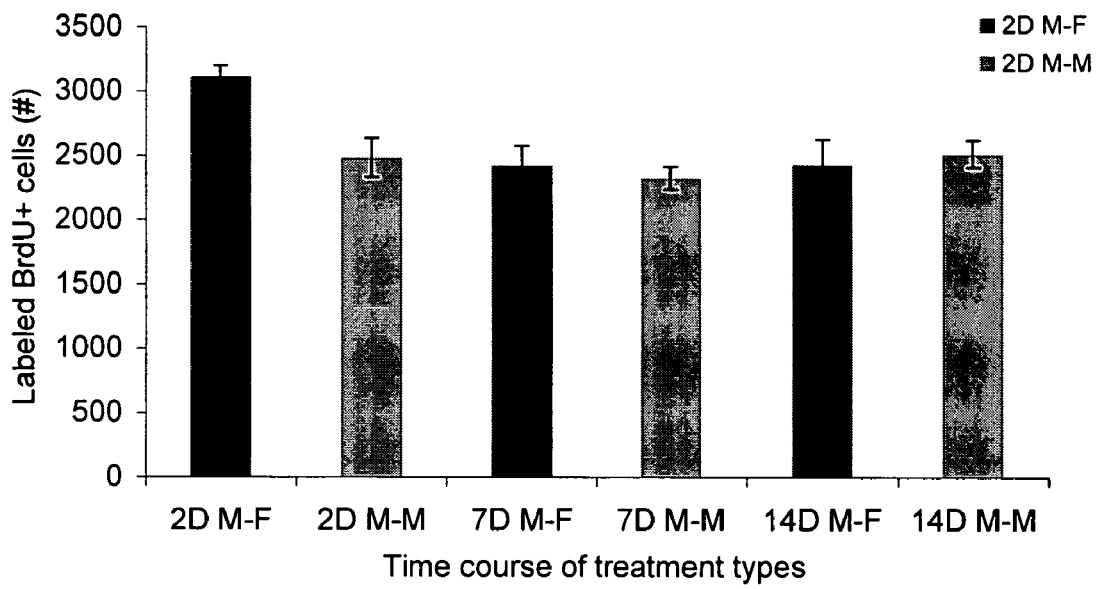

FIG. 2. The effects of female odors on proliferation of neural stem cells in the SVZ of male mice after an exposure of 2, 7 or 14 days. 2D, 7D and 14D indicate an exposure of 2, 7 and 14 days, respectively. M-F, male mice exposed to female odors; M-M, male mice exposed to male odors. The raw data are shown on the top of each panel.

(A) shows the effects on the number of BrdU positive cells in the SVZ.

(B) shows the effects on the number of Ki67 positive cells in the SVZ.

(C) shows the comparison of littermates and non-littermates.

Figure 3:
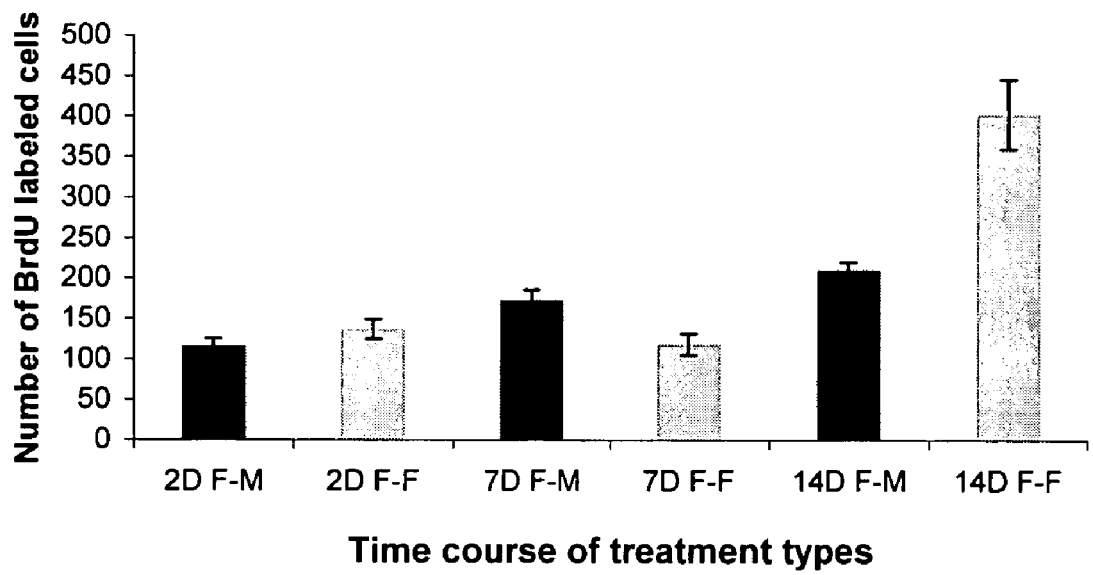

FIG. 3. The effects of male odors on proliferation of neural stem cells in the hippocampus of female mice after an exposure of 2, 7 or 14 days. 2D, 7D and 14D indicate an exposure of 2, 7 and 14 days, respectively. F-M, female mice exposed to male odors; F-F, female mice exposed to female odors. The raw data are shown on the top of each panel.

Figure 4:
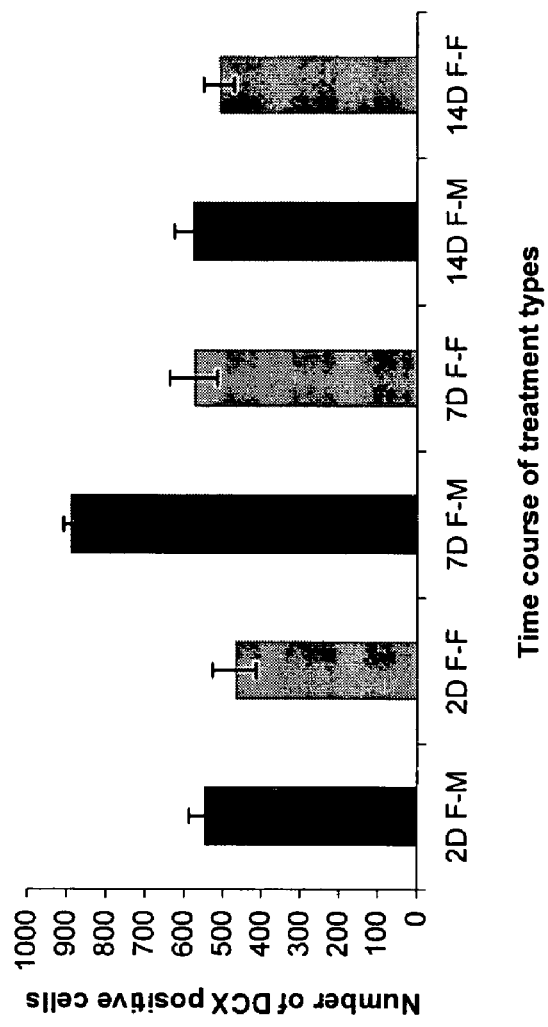

FIG. 4. The effects of male odors on neurogenesis in female mice after an exposure of 2, 7 or 14 days. 2D, 7D and 14D indicate an exposure of 2, 7 and 14 days, respectively. F-M, female mice exposed to male odors; F-F, female mice exposed to female odors. DCX, doublecortin. The raw data are shown on the top of each panel.

Figure 5:
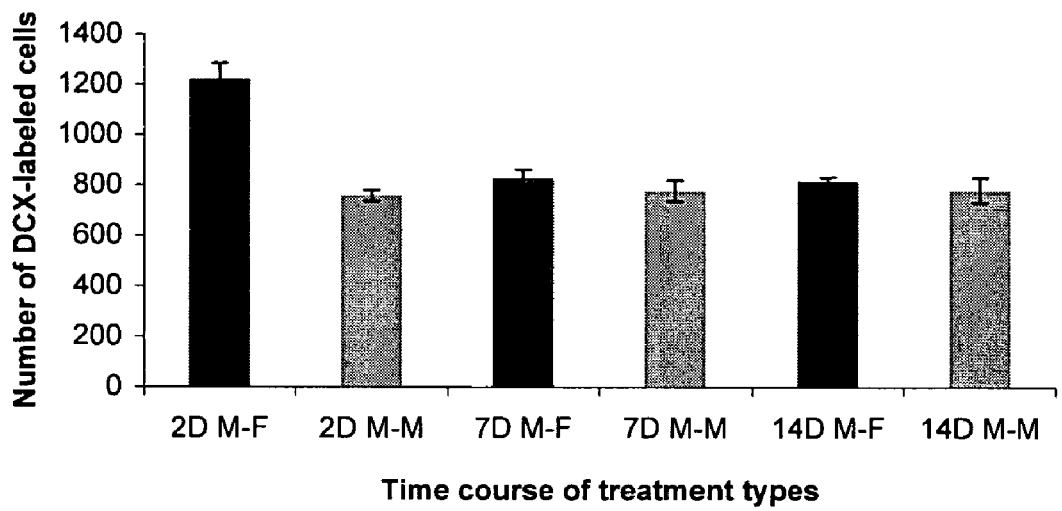

FIG. 5. The effects of female odors on neurogenesis in male mice after an exposure of 2, 7 or 14 days. 2D, 7D and 14D indicate an exposure of 2, 7 and 14 days, respectively.

M-F, male mice exposed to female odors; M-M, male mice exposed to male odors. DCX, doublecortin. The raw data are shown on the top of each panel.

Figure 6:
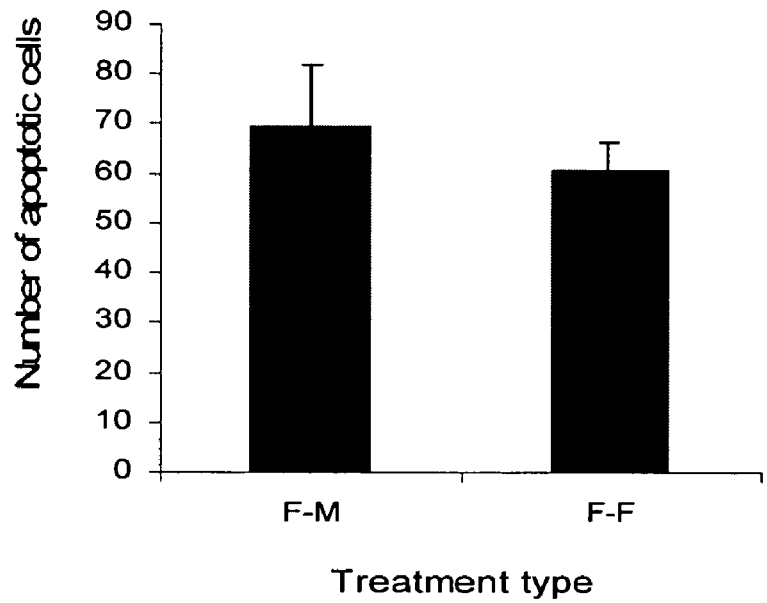
Figure 6:
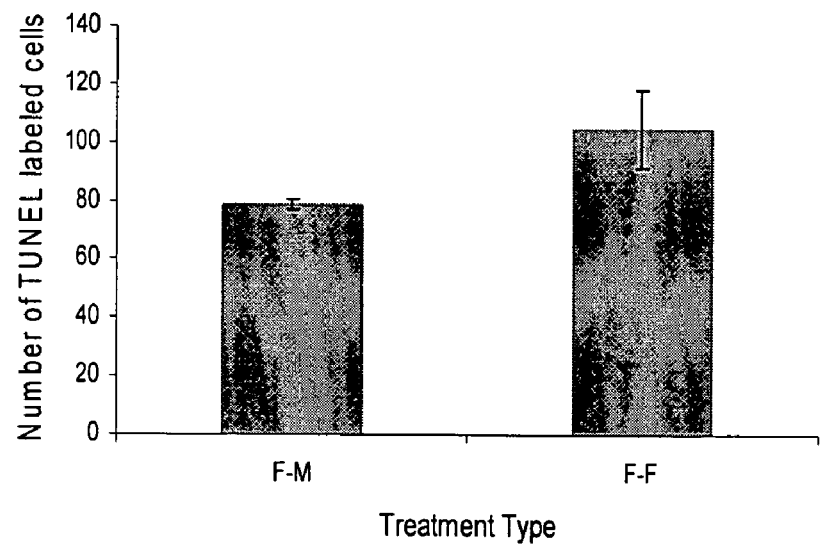

FIG. 6. The TUNEL (terminal deoxynucleotidyltransferase-mediated dUTP nick end labeling) assay. Female mice were exposed to male odors (F-M) or female odors (F-F) for 7 days, and the number of cells that underwent programmed cell death was determined by the TUNEL assay. (A) and (B) show the apoptotic cell counts in the SVZ and olfactory bulb, respectively.

Figure 7A:
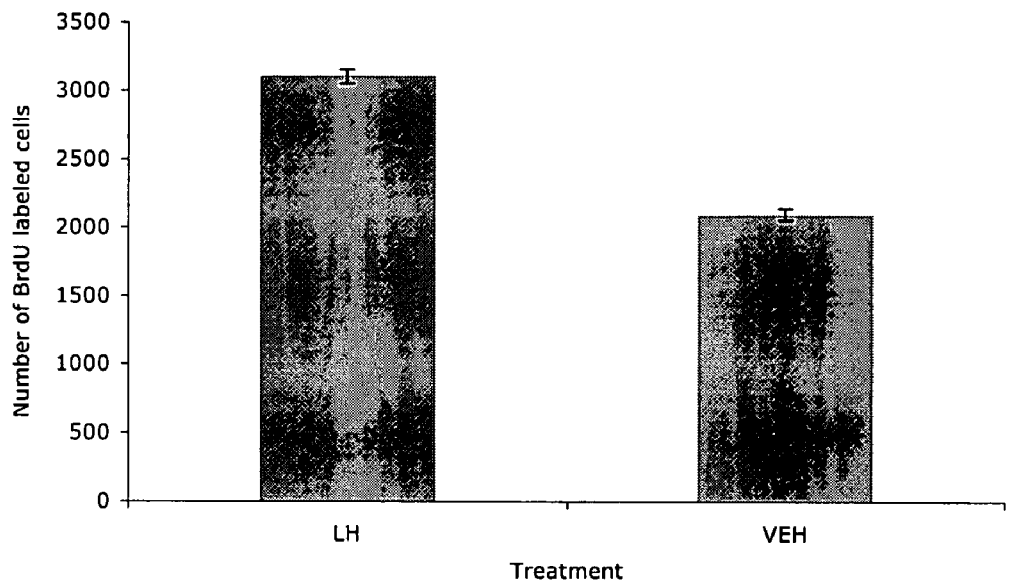
Figure 7B:
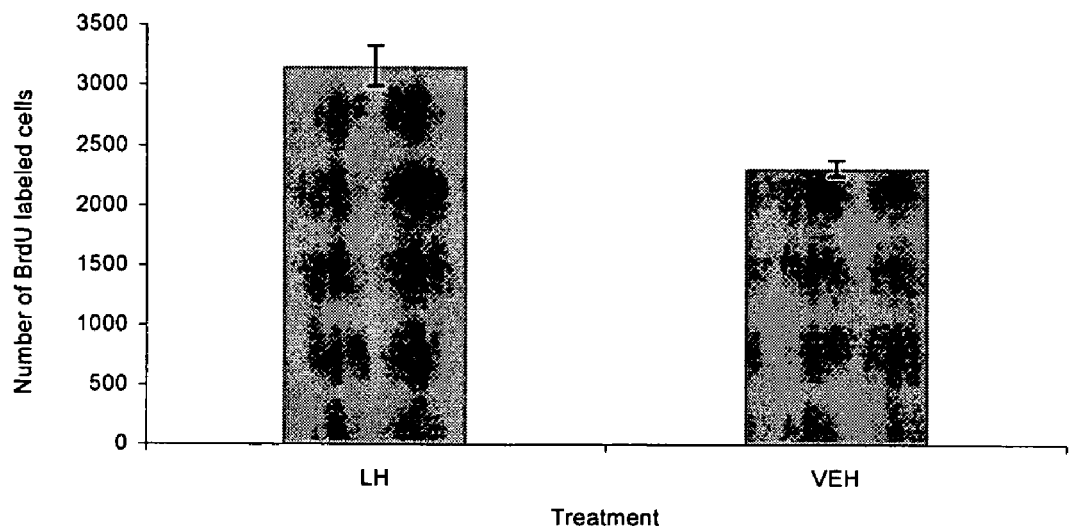

FIG. 7. The effects of LH on the number of BrdU positive cells in the SVZ in female mice. (A) and (B) show the effects of LH after a 2-day infusion (A) or 6-day infusion (B) of LH, respectively. VEH, vehicle.

Figure 8:
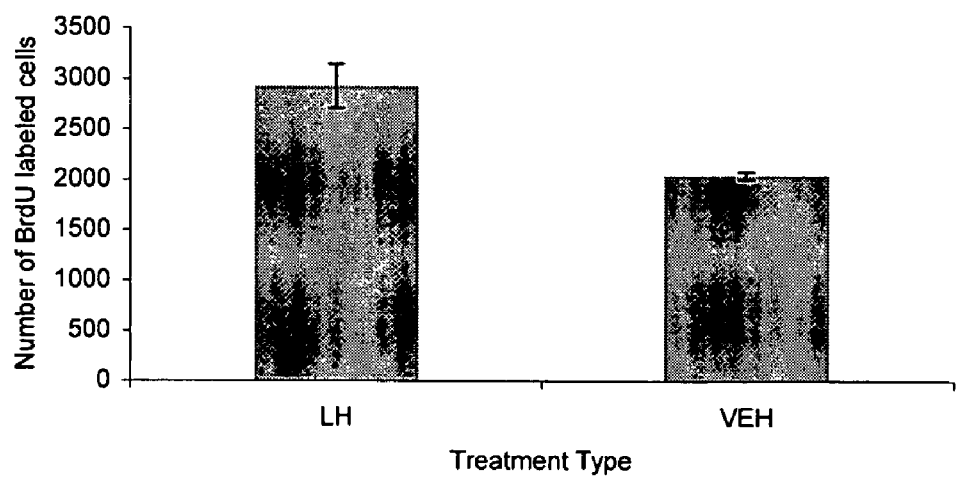

FIG. 8. The effects of LH on the number of BrdU positive cells in the SVZ in male mice after a 2-day infusion of LH. VEH, vehicle.

Figure 9:
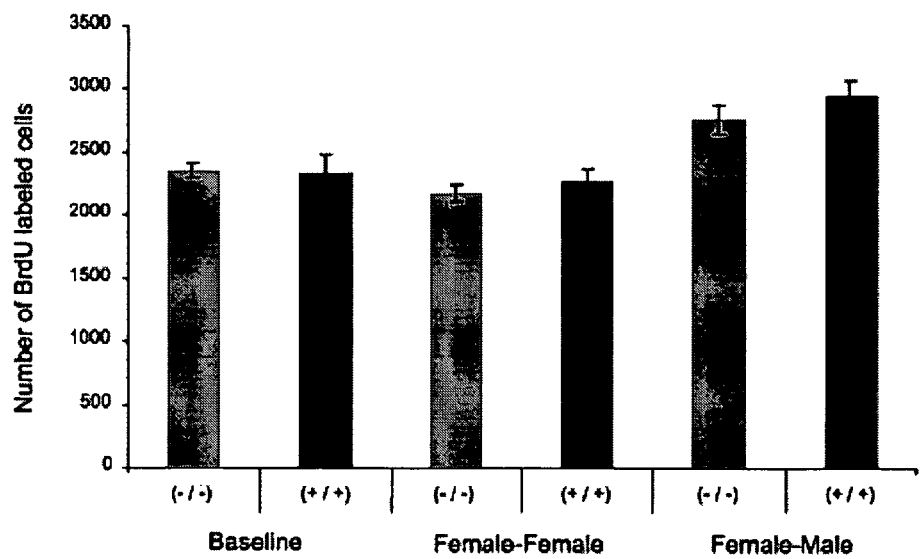
Figure 9:
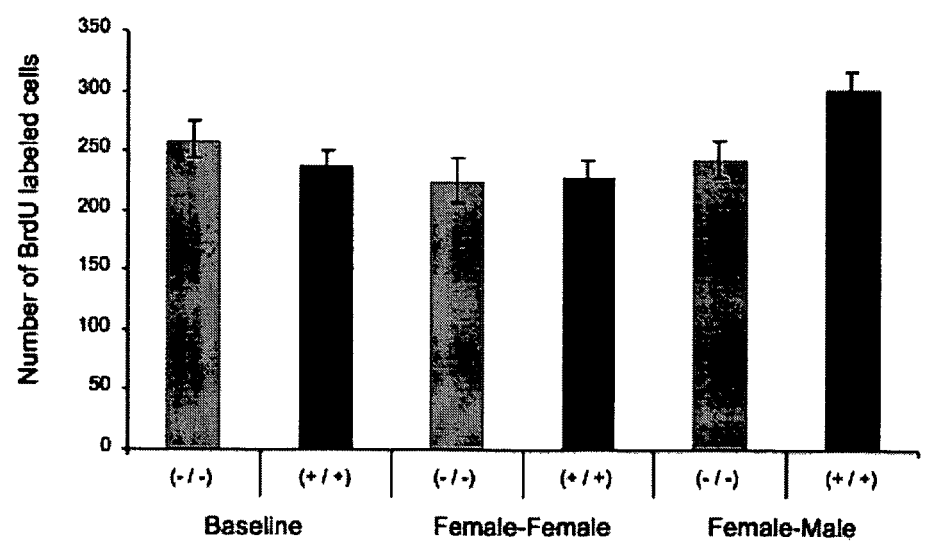

FIG. 9. The effects of LH receptors in pheromone-induced neural stem cell proliferation in female mice. (A) and (B) show the effects of LH receptor knock-out in the SVZ (A) and hippocampus (B), respectively. (−/−): LH receptor knock-out. (+/+): wild-type. Baseline: mice exposed to unodorized cages. Female-Female: female mice exposed to female odors. Female-Male: female mice exposed to male odors. $P^*<0.05$; LSD posthoc test.

Figure 10:
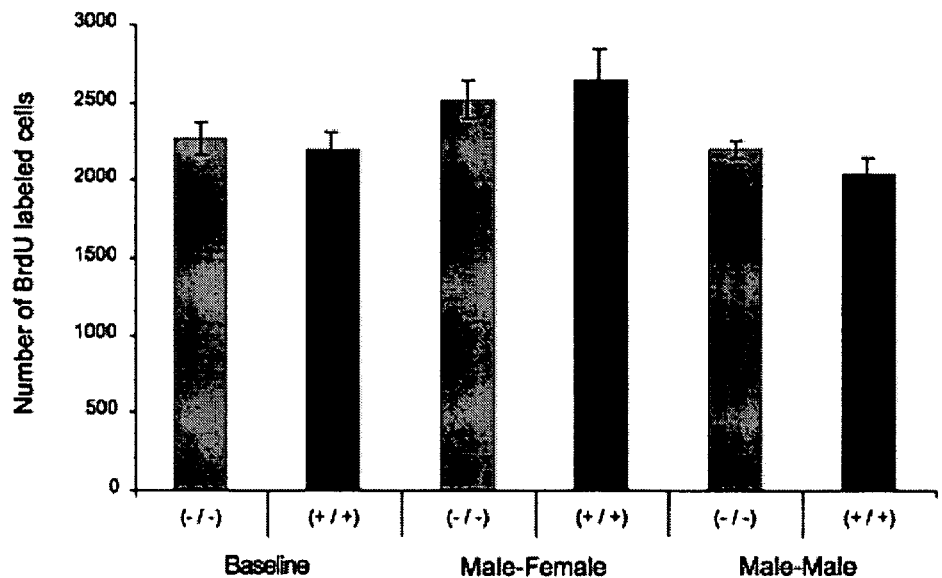
Figure 10:
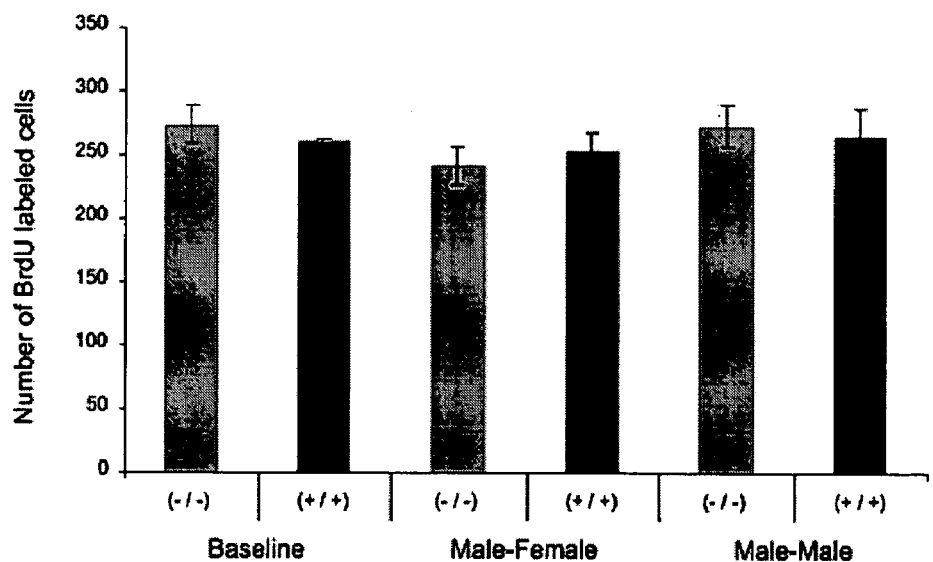

FIG. 10. The effects of LH receptors in pheromone-induced neural stem cell proliferation in male mice. (A) and (B) show the effects of LH receptor knock-out in the SVZ (A) and hippocampus (B), respectively. (−/−): LH receptor knock-out. (+/+): wild-type. Baseline: mice exposed to unodorized cages. Male-Female: male mice exposed to female odors. Male-Female: male mice exposed to female odors.

DETAILED DESCRIPTION OF THE INVENTION

The present invention provides a method of increasing neural stem cell numbers or neurogenesis by using a pheromone, a luteinizing hormone (LH) or a human chorionic gonadotrophin (hCG). The method can be practiced in vivo to obtain more neural stem cells in situ, which can in turn produce more neurons or glial cells to compensate for lost or dysfunctional neural cells. The method can also be practiced in vitro to produce a large number of neural stem cells in culture. The cultured stem cells can be used, for example, for transplantation treatment of patients or animals suffering from or suspected of having neurodegenerative diseases or conditions.

Prior to describing the invention in further detail, the terms used in this application are defined as follows unless otherwise indicated.

DEFINITIONS

A "neural stem cell" is a stem cell in the neural cell lineage. A stem cell is a cell which is capable of reproducing itself. In other words, daughter cells which result from stem cell divisions include stem cells. The neural stem cells are capable of ultimately differentiating into all the cell types in the neural cell lineage, including neurons, astrocytes and oligodendrocytes (astrocytes and oligodendrocytes are collectively called glia or glial cells). Thus, the neural stem cells referred to herein are multipotent neural stem cells.

A "neurosphere" or "sphere" is a group of cells derived from a single neural stem cell as the result of clonal expansion. A "primary neurosphere" refers to a neurosphere generated by plating as primary cultures brain tissue which contains neural stem cells. The method for culturing neural stem cells to form neurospheres has been described in, for example, U.S. Pat. No. 5,750,376. A "secondary neurosphere" refers to a neurosphere generated by dissociating primary neurospheres and allowing the individual dissociated cells to form neurospheres again.

A polypeptide which shares "substantial sequence similarity" with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level.

The phrase "percent identity" or "% identity" of an analog or variant with a native factor refers to the percentage of amino acid sequence in the native factor which are also found in the analog or variant when the two sequences are aligned. Percent identity can be determined by any methods or algorithms established in the art, such as LALIGN or BLAST.

A polypeptide possesses a "biological activity" of a native factor if it is capable of binding to the receptor for the native factor or being recognized by a polyclonal antibody raised against the native factor. Preferably, the polypeptide is capable of specifically binding to the receptor for the native factor in a receptor binding assay.

A "functional agonist" of a native factor is a compound that binds to and activates the receptor of the native factor, although it does not necessarily share a substantial sequence similarity with the native factor.

An "LH" is a protein which (1) comprises a polypeptide that shares substantial sequence similarity with a native mammalian LH, preferably the native human LH; and (2) possesses a biological activity of the native mammalian LH. The native mammalian LH is a gonadotropin secreted by the anterior lobe of the pituitary. LH is a heterodimer consisting of non-covalently bound alpha and beta subunits. The alpha subunit is common among LH, FSH and hCG, and the beta subunit is specific for each hormone. The LH useful in the present invention may have the native alpha subunit, with the beta subunit sharing a substantial sequence similarity with a native mammalian LH. Alternatively, the LH may have the native beta subunit, with the alpha subunit sharing a substantial sequence similarity with a native mammalian LH. The LH may also have both the alpha and beta subunit sharing a substantial sequence similarity with a native, corresponding subunit. Thus, the term "LH" encompasses LH analogs which comprise a deletional, insertional, or substitutional mutants of a native LH subunit. Furthermore, the term "LH" encompasses the LHs from other species and the naturally occurring variants thereof. In addition, an "LH" may also be a functional agonist of a native mammalian LH receptor.

An "hCG" is a protein which (1) comprises a polypeptide that shares substantial sequence similarity with the native hCG; and (2) possesses a biological activity of the native hCG. The native hCG is a heterodimer consisting of non-covalently bound alpha and beta subunits. The alpha subunit is common among LH, FSH and hCG, and the beta subunit is specific for each hormone. However, the beta subunits of hCG and LH shares a 85% sequence similarity. The hCG useful in the present invention may have the native alpha subunit, with the beta subunit sharing a substantial sequence similarity with the native hCG. Alternatively, the hCG may have the native beta subunit, with the alpha subunit sharing a substantial sequence similarity with the native hCG. The hCG may also have both the alpha and beta subunit sharing a substantial sequence similarity with the native, corresponding subunit. Thus, the term "hCG" encompasses hCG analogs which comprise a deletional, insertional, or substitutional mutants of a native hCG subunit. Furthermore, the term "hCG" encompasses the hCG counterparts from other species and the naturally occurring variants thereof. In addition, an "hCG" may also be a functional agonist of a native mammalian hCG/LH receptor.

A "prolactin" is a polypeptide which (1) shares substantial sequence similarity with a native mammalian prolactin, preferably the native human prolactin; and (2) possesses a biological activity of the native mammalian prolactin. The native human prolactin is a 199-amino acid polypeptide synthesized mainly in the pituitary gland. Thus, the term "prolactin" encompasses prolactin analogs which are the deletional, insertional, or substitutional mutants of the native prolactin. Furthermore, the term "prolactin" encompasses the prolactins from other species and the naturally occurring variants thereof.

In addition, a "prolactin" may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode et al., 1996); or a ligand for the prolactin receptor as described in U.S. Pat. Nos. 5,506,107 and 5,837,460.

An "EGF" means a native EGF or any EGF analog or variant that shares a substantial amino acid sequence similarity with a native EGF, as well as at least one biological activity with the native EGF, such as binding to the EGF receptor. Particularly included as an EGF is the native EGF of any species, TGF.alpha., or recombinant modified EGF. Specific examples include, but are not limited to, the recombinant modified EGF having a deletion of the two C-terminal amino acids and a neutral amino acid substitution at position 51 (particularly EGF51 gln51; U.S. Patent Application Publication No. 20020098178A1), the EGF mutein (EGF-X.sub.6) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg—Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

In addition, an "EGF" may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, 1985 and U.S. Pat. No. 5,723,115).

A "PACAP" means a native PACAP or any PACAP analog or variant that shares a substantial amino acid sequence similarity with a native PACAP, as well as at least one biological activity with the native PACAP, such as binding to the PACAP receptor. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

In addition, a "PACAP" may also be a functional agonist of a native mammalian PACAP receptor. For example, the functional agonist may be maxadilan, a polypeptide that acts as a specific agonist of the PACAP type-1 receptor (Moro et al., 1997).

An "erythropoietin (EPO)" means a native EPO or any EPO analog or variant that shares a substantial amino acid sequence similarity with a native EPO, as well as at least one biological activity with the native EPO, such as binding to the EPO receptor. Erythropoietin analogs and variants are disclosed, for example, in U.S. Pat. Nos. 6,048,971 and 5,614,184.

In addition, an "EPO" may also be a functional agonist of a native mammalian EPO receptor. For example, the functional agonist may be EMP1 (EPO mimetic peptide 1, Johnson et al., 2000); one of the short peptide mimetics of EPO as described in Wrighton et al., 1996 and U.S. Pat. No. 5,773,569; any small molecular EPO mimetic as disclosed in Kaushansky, 2001; an antibody that activates the EPO receptor as described in U.S. Pat. No. 5,885,574, WO 96/40231, WO 97/48729, Fernandez-Pol, 1985 or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952), or a ligand for the EPO receptor as described in U.S. Pat. Nos. 5,506,107 and 5,837,460.

A "LH/hCG-inducing agent" is a substance that, when given to an animal, is capable of increasing the amount of LH or hCG in the animal. For example, LH releasing hormone (LHRH) stimulates the secretion of LH.

A "pheromone" is a substance that serves as a signal to another animal of the same species, usually of the opposite gender. A mammalian pheromone can be a protein a small molecule. Preferably, the pheromone is selected from the group consisting of 2-sec-butyl-4,5-dihydrothiazole (SBT), 2,3-dehydro-exo-brevicomin (DHB), alpha and beta farnesenes, 6-hydroxy-6-methyl-3-heptanone, 2-heptanone, trans-5-hepten-2-one, trans-4-hepten-2-one, n-pentyl acetate, cis-2-penten-1-yl-acetate, 2,5-dimethylpyrazine, dodecyl propionate, and (Z)-7-dodecen-1-yl acetate (see, e.g., Dulac et al., 2003).

"Enhancing" the formation of a cell type means increasing the number of the cell type. Thus, an agent can be used to enhance neuron formation if the number of neurons in the presence of the agent is larger than the number of neurons absent the agent. The number of neurons in the absence of the agent may be zero or more.

A "neurodegenerative disease or condition" is a disease or medical condition associated with neuron loss or dysfunction. Examples of neurodegenerative diseases or conditions include neurodegenerative diseases, CNS injuries or CNS dysfunctions. Neurodegenerative diseases include, for example, Alzheimer's disease, macular degeneration, glaucoma, diabetic retinopathy, peripheral neuropathy, Huntington's disease, amyotrophic lateral sclerosis, and Parkinson's disease. CNS injuries include, for example, stroke (e.g., hemorrhagic stroke, focal ischemic stroke or global ischemic stroke) and traumatic brain or spinal cord injuries (e.g. injuries caused by a brain or spinal cord surgery or physical accidents). CNS dysfunctions include, for example, depression, epilepsy, neurosis and psychosis.

"Treating or ameliorating" means the reduction or complete removal of the symptoms of a disease or medical condition.

A mammal "suspected of having a neurodegenerative disease or condition" is a mammal which is not officially diagnosed with the neurodegenerative disease or condition but shows a symptom of the neurodegenerative disease or condition, is susceptible to the neurodegenerative disease or condition due to family history or genetic predisposition, or has previously had the neurodegenerative disease or condition and is subject to the risk of recurrence.

"Transplanting" a composition into a mammal refers to introducing the composition into the body of the mammal by any method established in the art. The composition being introduced is the "transplant", and the mammal is the "recipient". The transplant and the recipient may be syngeneic, allogeneic or xenogeneic. Preferably, the transplantation is an autologous transplantation.

An "effective amount" is an amount of a therapeutic agent sufficient to achieve the intended purpose. For example, an effective amount of an LH or hCG to increase the number of neural stem cells is an amount sufficient, in vivo or in vitro, as the case may be, to result in an increase in neural stem cell number. An effective amount of an LH or hCG to treat or ameliorate a neurodegenerative disease or condition is an amount of the LH/hCG sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Methods

Neural stem cells are located in two regions of the adult mammalian brain (Reynolds and Weiss, 1992): the dendate gyrus of the hippocampus and the subventricular zone (SVZ) of the lateral ventricles (Luskin 1993; Menezes et al., 1995; Frisen et al., 1998; Peretto et al., 1999; Gage, 2000; Rochefort et al., 2002). Neural stem cells follow two mitotic pathways that contribute to their growth and proliferation. The first mitotic path is where neural stem cells divide symmetrically as a means of regeneration and self-renewal. The second mitotic division is asymmetrical, which results in a daughter neural stem cell and a progenitor cell. It is ultimately the progenitor cell that takes on a terminalistic fate as one of the cell types of the central nervous system. For example, in the case of neurogenesis, it is the neuronal progenitor cell that gives rise to a neuron (Weiss et al., 1996; Morrison and Shah, 1997; Peretto et al., 1999; Rao, 1999).

The neuronal progenitors of the hippocampus reside in the dentate gyrus and have the ability to proliferate and migrate to the granular cell layer to differentiate into granule cells (Nilsson et al., 1999; Gage 2000; Rochefort et al., 2002). In the SVZ, neural stem cells and progenitors proliferate, then the progenitors follow a migratory path, known as the rostral migratory stream (RMS), where they are destined for the olfactory bulb (OB) to become interneurons (Luskin 1993; Menezes et al., 1995; Rao, 1999; Rochefort et al., 2002).

It has been shown that an enriched olfactory environment, created with novel odors, increased neurogenesis in the olfactory bulb and improved odor memory (Rochefort et al., 2002). Although the olfactory bulb interneurons are derived from the neural stem cells in the SVZ, exposure to the enriched olfactory environment had no effect on cell proliferation in the SVZ (Rochefort et al., 2002). As described in the present invention, however, we observed the surprising effects of male and female odors on the opposite gender in neural stem cell proliferation and neurogenesis.

Figure 1A:
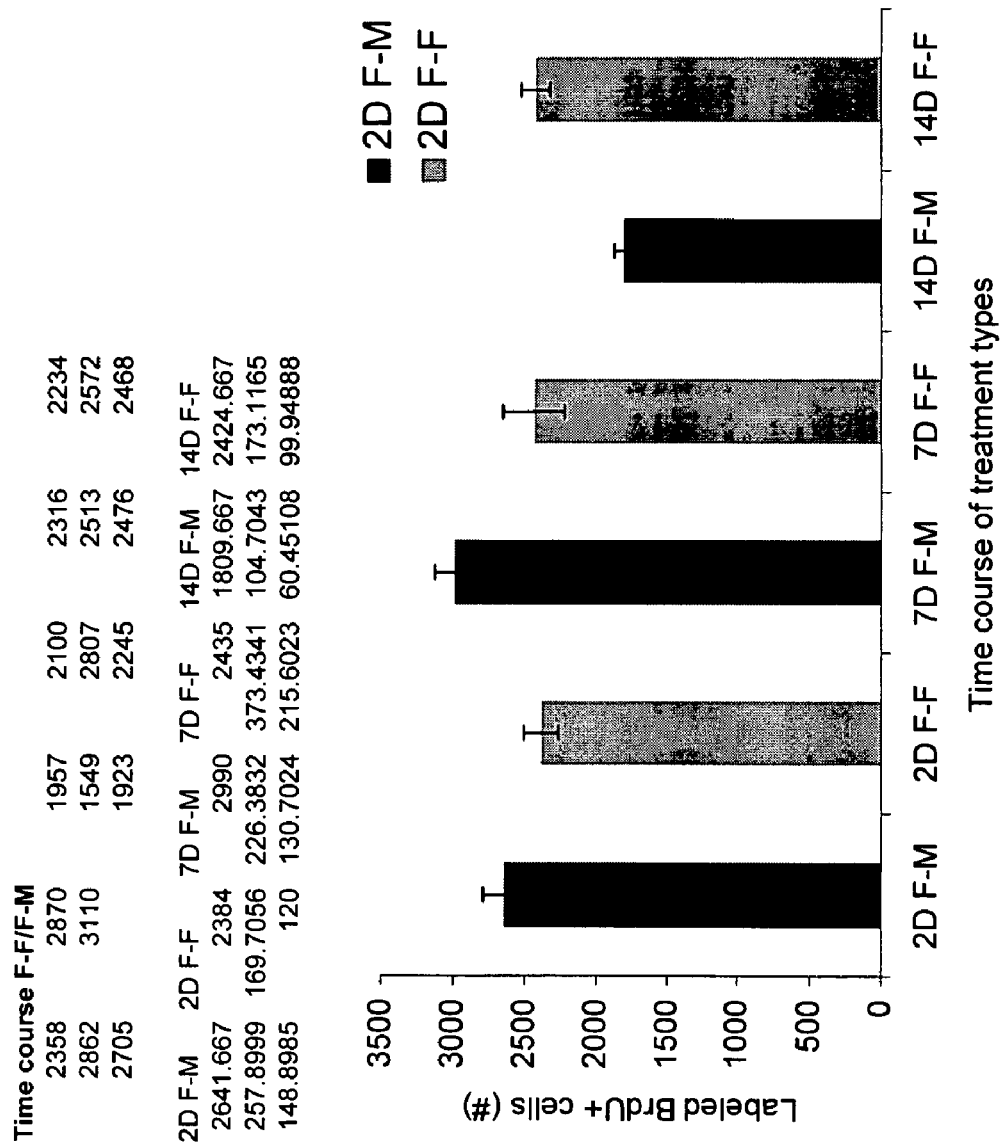
FIG. 1. The effects of male odors on proliferation of neural stem cells in the SVZ of female mice after an exposure of 2, 7 or 14 days. 2D, 7D and 14D indicate an exposure of 2, 7 and 14 days, respectively. F-M, female mice exposed to male odors; F-F, female mice exposed to female odors. The raw data are shown on the top of each panel.
Figure 1B:
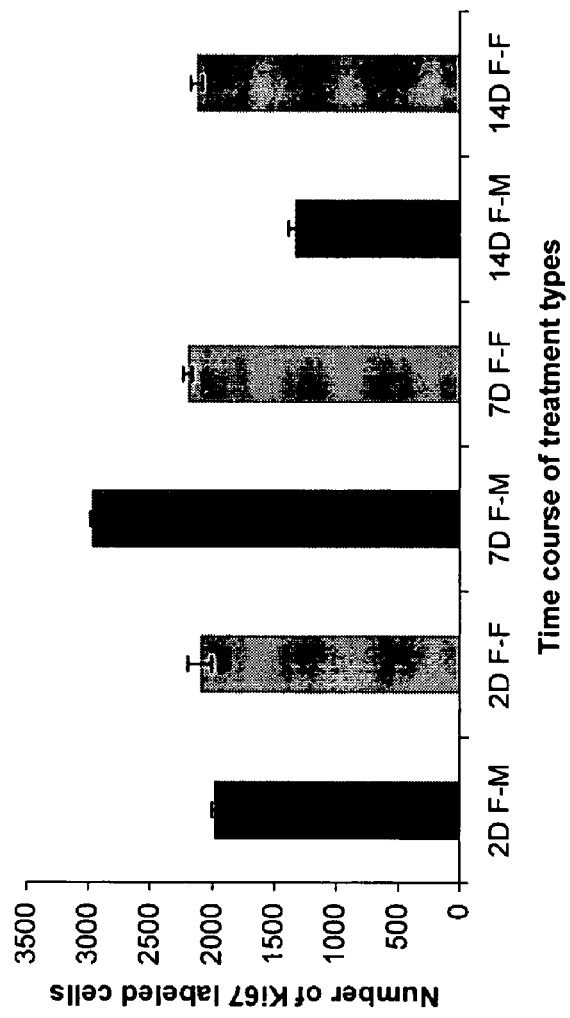

To determine the impact of male or female odors, adult mice were exposed to the odors of the opposite gender for 2 days, 7 days or 14 days. A control group was exposed to the odors of the same gender for the same period of time. The mice then received BrdU to label proliferating cells, and the locations of the BrdU positive cells were identified by immunohistochemical studies (Example 1). As shown in FIG. 1A, proliferating cells in the SVZ of female mice remained at the same level after being exposed to female odors for 2, 7 or 14 days. In the female group exposed to male odors, however, proliferating cells in the SVZ changed with time: increased significantly after 7 days and decreased significantly after 14 days. A 2-day exposure had no significant effect. The same pattern was observed when Ki67 was used to label proliferating cells (FIG. 1B), indicating that the change in BrdU positive cells reflected a change of proliferation level.

Figure 2B:
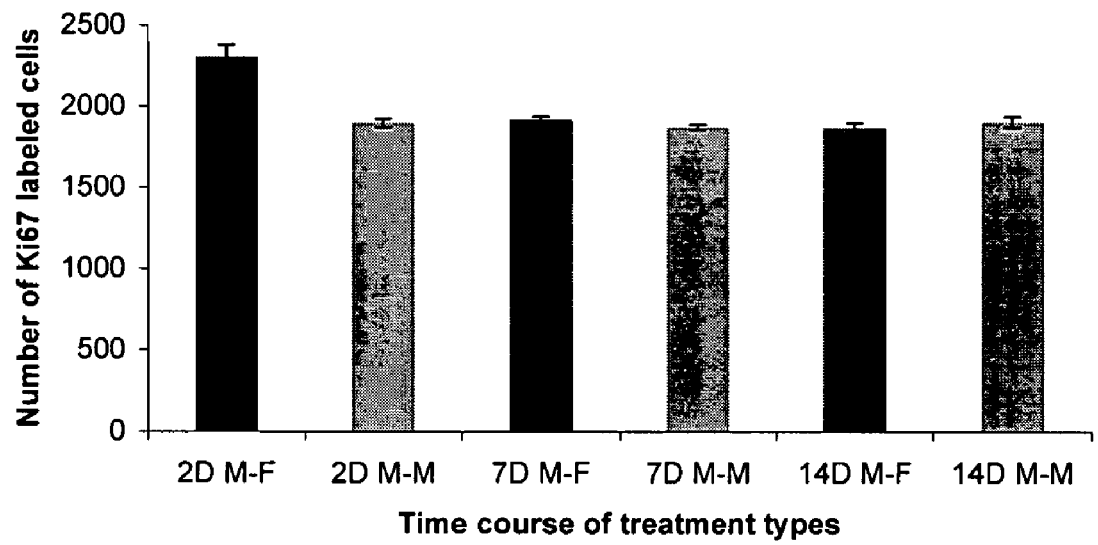

Female odors also affected proliferation in male mouse brains, but in a different temporal pattern. When males were exposed to female odors for 2 days, there was a sudden increase in the number of BrdU positive cells (FIG. 2A) or Ki67 positive cells (FIG. 2B). After a 7 or 14 day exposure, however, the number of newly proliferated cells decreased to the control level.

Strikingly, the neural stem cells in the hippocampus also responded to gender-specific odors. Again, exposure for two days to male odors had no significant effects on female mice, but a 7-day exposure resulted in a significant increase in proliferation in the hippocampus (FIG. 3). After an exposure for 14 days, levels of proliferating cells were significantly lower in females exposed to male odors when compared with the females that had been exposed to female odors. To our knowledge, this is the first time that any stimulus, other than growth factors (e.g., EGF plus FGF), has been shown to exert the same effects on the neural stem cells in the SVZ and the hippocampus. Usually the effects are opposite. For example, prolactin affects the SVZ but not the hippocampus (Shingo et al., 2003); estrogen stimulates proliferation in the hippocampus but not in the SVZ (Tanapat et al., 1999); an enriched environment and physical activities promote hippocampal neurogenesis, but not SVZ neurogenesis (Brown et al., 2003).

Neurogenesis was also enhanced upon exposure to the odors of the opposite gender (Example 2). Thus, tissue sections from the animals described above were stained for doublecortin, a cytoplasmic protein expressed in neuronal progenitor cells, to determine the extent of neurogenesis in the mice described above. As in the case of proliferating cells, female mice had significantly more doublecortin positive cells after a 7-day exposure to male odors (FIG. 4) while male mice had significantly more doublecortin positive cells after a 2-day exposure to female odors (FIG. 5).

To determine if pheromones from the opposite gender also impact survival of neural cells, the TUNEL assay was performed. The results indicate that no significant difference can be observed in the SVZ (FIG. 6A) or olfactory bulb (FIG. 6B) of female mice after a 7-day exposure to male odors.

Male pheromones are known to increase the levels of the luteinizing hormone (LH) and decrease the levels of prolactin, while female pheromones are associated with an increase in prolactin (Dulac et al., 2003). In an attempt to investigate how pheromones enhance neural stem cell proliferation and neurogenesis in the opposite gender, animals were infused with LH. The results show that LH increase proliferation significantly in the SVZ of both female (FIGS. 7A and 7B) and male mice (FIG. 8). Consistent with these results, LH is also capable of increasing self-renewal of neural stem cells in culture (Example 3).

Accordingly, the present invention provides a method of increasing neural stem cells numbers either in vivo or in vitro using a pheromone and/or LH. Human chorionic gonadotrophin (hCG) is expected to have the same effect as LH as hCG is an analog of, and shares the same receptor with, LH. When used to increase neural stem cell number in vivo, this method will result in a larger pool of neural stem cells in the brain. This larger pool of neural stem cells can subsequently generate more neural cells, particularly neurons or glial cells, than would a population of stem cells without pheromone, LH/hCG. The neural cells, in turn, can compensate for lost or degenerate neural cells which are associated with neurodegenerative diseases and conditions, including nervous system injuries.

LH/hCG or other factors induced by pheromones can also be used to increase neural stem cell numbers in vitro. The resulting stem cells can be used to produce more neurons and/or glial cells in vitro, or used in transplantation procedures into humans or animals suffering from neurodegenerative diseases or conditions. It is preferable that neural stem cells produced according to the present invention, rather than neurons or glial cells, are transplanted. Once neural stem cells are transplanted, growth and/or differentiation agents can be administered in vivo to further increase the number of stem cells, or to selectively enhance neuron formation or glial cell formation. The additional agents can likewise be used in vitro with LH or hCG, or administered in vivo in combination with pheromone/LH/hCG.

Exemplary differentiation agents include, but are not limited to:

1. Erythropoeitin (Epo): It has been demonstrated that Epo enhances NSC commitment to neuronal cell lineage and that this can be used to treat mouse and rat models of stroke.
2. Brain derived neurotrophic factor (BDNF): BDNF is a known survival factor and differentiation agent that promotes the neuronal lineage.
3. Transforming growth factor beta and bone morphogenetic proteins (BMPs): BMPs are known differentiation agents that promote the neuronal lineage and the generation of specific neuronal phenotypes (e.g.: sensory interneurons in the spinal cord).
4. Thyroid hormone (TH, including both the T3 and T4 forms): TH is known as a differentiation agent that promotes the maturation and generation of oligodendroctyes. See, e.g., (Rodriguez-Pena, 1999).
5. Thyroid stimulating hormone (TSH) and Thyroid releasing hormone (TRH): TSH/TRH promote the release of TH from the anterior pituitary resulting in increased levels of circulating TH. This agent could be used in combination with pheromone/LH/hCG to promote oligodendrogliogenesis from NSCs.
6. Sonic hedgehog (SHH): SHH is a morphogen that patterns the developing CNS during development and, in different concentrations, promotes the generation of specific types of neurons (eg: motoneurons in the spinal cord) and oligodendrocytes. This agent could be used in combination with pheromone/LH/hCG to promote neurogenesis and/or oligodendrogliogenesis from NSCs.
7. Platelet derived growth factor (PDGF): PDGF promotes the generation and differentiation of oligodendrocytes from NSCs. This agent could be used in combination with pheromone/LH/hCG to promote oligodendrogliogenesis from NSCs.
8. Cyclic AMP and agents which enhance the cAMP pathway, such as pituitary adenylate cyclase activating polypeptide (PACAP) and serotonin, are also good candidates for selectively promoting neuron production.

Agents that can increase neural stem cell number include, without being limited to:

9. Follicle-stimulating hormone (FSH) often acts in concert with LH; known to induce LH receptor expression and can therefore enhance the effects of LH signaling.
10. Growth hormone (GH) can stimulate NSC proliferation.
11. Insulin growth factors (IGFs) are somatomedians that are released from many tissues in response to GH and mediate many of the growth promoting effects of GH. IGF-1 stimulates NSC proliferation.
12. Growth hormone releasing hormone (GHRH) are secreted from the hypothalamus and induces GH release from the anterior pituitary, resulting in increased levels of circulating GH.
13. Prolactin (PRL) is secreted from the anterior pituitary and known to promote NSC proliferation. PRL and pheromone/LH/hCG may be used in combination to maximize NSC proliferation.
14. Prolactin releasing peptide (PRP) triggers the release of prolactin and can be used in combination with pheromone/LH/hCG to maximize NSC proliferation.
15. Fibroblast growth factor is a known mitogenic agent for NSCs.
16. Estrogen is known to promote the proliferation of NSCs in the hippocampus.
17. Serotonin is known to promote the proliferation of NSCs in the hippocampus.
18. Epidermal growth factor is a known mitogenic agent for NSCs.
19. Transforming growth factor alpha (TGFalpha) is a known mitogenic agent for NSCs.
20. Gonadotropin releasing hormone (GnRH) triggers the release of LH and could be used in combination with or in place of pheromone/LH/hCG to increase circulating levels of LH and enhance NSC proliferation.
21. Ciliary neurotrophic factor and leukemia inhibitory factor: Both of these agents, and others, signal via the gp130 subunit. This signaling pathway has been demonstrated to promote NSC self-renewal, thereby expanding the NSC population of the brain. These agents could be used in combination with pheromone/LH/hCG to promote NSC proliferation and increase the size of the NSC population within the CNS.

Further provided by the present invention are methods of increasing neuron formation from neural stem cells in vitro or in vivo. In particular, methods of enhancing new olfactory neuron production are provided.

The increase in neural stem cells or neurons is preferably at least about 10%, more preferably at least about 20%, even more preferably at least about 30%, yet more preferably at least about 40%, still more preferably at least about 50%, and further more preferably at least about 60%. Most preferably, the increase is at least about 80%.

The present invention also provides a method for treating or ameliorating a neurodegenerative disease or condition in an animal, particularly a mammal. This can be achieved, for example, by administering an effective amount of an LH and/or hCG to the mammal, or transplanting to the mammal neural stem cells, progenitor cells derived from neural stem cells, neurons and/or glial cells produced according to the present invention. Preferably, neural stem cells are transplanted. In addition to the transplantation, LH/hCG and/or additional agents can be further provided to the transplantation recipient, particularly concurrently with or after the transplantation.

One particularly interesting neurodegenerative condition is aging. We have found that the number of neural stem cells in the subventricular zone is significantly reduced in aged mice. Accordingly, it will be of particular interest to ameliorate problems associated with aging by increasing neural stem cell numbers with pheromone/LH/hCG.

For example, the neural stem cell in the subventricular zone is the source of olfactory neurons, and olfactory dysfunction is a hallmark of forebrain neurodegenerative diseases, such as Alzheimer's, Parkinson's and Huntington's diseases. Disruption of neuronal migration to the olfactory bulb leads to deficits in olfactory discrimination, and doubling the new olfactory interneuons enhances new odor memory (Rochefort et al., 2002). Therefore, pheromone/LH/hCG can be used to enhance olfactory discrimination or olfactory memory, as well as physiological functions that are associated with olfaction and olfactory discrimination, such as mating, offspring recognition and rearing.

Another particularly important application of the present invention is the treatment and/or amelioration of CNS injuries, such as stroke.

Compositions

The present invention provides compositions that comprise a pheromone, LH or hCG and optionally at least one additional agent. The additional agent is capable of increasing neural stem cell number or enhancing neural stem cell differentiation to neurons or glial cells, as described above. The additional agent is preferably selected from the group consisting of follicle-stimulating hormone (FSH), gonadotropin releasing hormone (GnRH), prolactin, prolactin releasing peptide (PRP) erythropoietin, cyclic AMP, pituitary adenylate cyclase activating polypeptide (PACAP), serotonin, bone morphogenic protein (BMP), epidermal growth factor (EGF), transforming growth factor alpha (TGFalpha), transforming growth factor beta (TGFbeta), fibroblast growth factor (FGF), estrogen, growth hormone, growth hormone releasing hormone, insulin-like growth factors, leukemia inhibitory factor, ciliary neurotrophic factor (CNTF), brain derived neurotrophic factor (BDNF), thyroid hormone, thyroid stimulating hormone, sonic hedgehog (SHH), and/or platelet derived growth factor (PDGF). Most preferably, erythropoietin, prolactin, EGF and/or PACAP are added.

The pheromone can be any pheromone that is capable of increasing neural stem cell numbers in the mammal. Assays for determining if a substance is capable of increasing neural stem cell numbers are established in the art and described herein (e.g., see Examples 1 and 3). The pheromone is preferably selected from the group consisting of 2-sec-butyl-4,5-dihydrothiazole (SBT), 2,3-dehydro-exo-brevicomin (DHB), alpha and beta farnesenes, 6-hydroxy-6-methyl-3-heptanone, 2-heptanone, trans-5-hepten-2-one, trans-4-hepten-2-one, n-pentyl acetate, cis-2-penten-1-yl-acetate, 2,5-dimethylpyrazine, dodecyl propionate, and (Z)-7-dodecen-1-yl acetate (see, e.g., Dulac et al., 2003).

The LH/hCG useful in the present invention includes any LH or hCG analog or variant which is capable of increasing neural stem cell number. A LH/hCG analog or variant comprises a protein which contains at least about 30% of the amino acid sequence of at least one subunit of the native human LH or hCG, and which possesses a biological activity of the native LH or hCG. Preferably, the biological activity of LH or hCG is the ability to bind the LH/hCG receptors. Specifically included as LH/hCG are the naturally occurring LH/hCG variants; LH/hCG counterparts from various mammalian species, including but not limited to, human, other primates, rat, mouse, sheep, pig, and cattle; and the commonly used analogs listed in Table 1 below. GnRH, or an analog thereof, can be used in the place of or in addition to LH/hCG.

TABLE 1

Common Analogs of GnRH, LH and hCG

GnRH/LHRH agonists

GnRH agonist, leuprorelin (pGlu-His-Trp-Ser-Tyr-D-Leu-Leu-Arg-Pro-NHEt)
Buserelin another LH-RH agonist
Serophene: A prescription medication that initiates the release of GnRH
LH Luveris ® (lutropin alfa) pure luteinizing hormone (recombinant human LH)
hCG Ovidrel ®/Ovitrelle ® 1 (choriogonadotropin alfa);
recombinant chorionic gonadotropin (r-hCG)
Pregnyl ® is an injectable, highly purified preparation of human chorionic gonadotropin obtained from the urine of pregnant women. Pregnyl has been in use throughout the world since 1932.
NOVAREL ™ (chorionic gonadotropin for injection, USP)
Profasi: human chorionic gonadotropin (hCG). Profasi is administered intramuscularly.

Similarly, any additional compounds or agents that are useful in the present invention include their analogs and variants that share a substantial similarity and at least one biological activity with the native compounds or agents. For example, EGF can be used in conjunction with LH/hCG in the present invention. In addition to native EGF, an EGF analog or variant can also be used, which should share a substantial amino acid sequence similarity with the native EGF, as well as at least one biological activity with the native EGF, such as binding to the EGF receptor. Particularly included as an EGF is the native EGF of any species, TGFalpha, or recombinant modified EGF. Specific examples include, but are not limited to, the recombinant modified EGF having a deletion of the two C-terminal amino acids and a neutral amino acid substitution at position 51 (particularly EGF51 gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg—Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

As another example, PACAP can also be used in conjunction with LH/hCG. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

Erythropoietin analogs and variants are disclosed, for example, in U.S. Pat. Nos. 6,048,971 and 5,614,184.

Further contemplated in the present invention are functional agonists of LH/hCG or additional agents useful in the present invention. These functional agonists bind to and activate the receptor of the native agent, although they do not necessarily share a substantial sequence similarity with the native agent. For example, maxadilan is a polypeptide that acts as a specific agonist of the PACAP type-1 receptor (Moro et al., 1997).

ing and preparing ligands for receptors, e.g., EPO and prolactin receptors, are described, for example, in U.S. Pat. Nos. 5,506,107 and 5,837,460.

Commonly used analogs of certain additional agents can also be found in Table 2 below:

TABLE 2

Common Analogs of Additional Agents

FSH

Follitropin beta, Follistim/Puregon ®, recombinant follicle-stimulating hormone (FSH), pure gonadotropin widely used to treat infertility; launched by Organon in 1996
GONAL-f ™ (follitropin alpha) is recombinant human follicle-stimulating hormone, which is equivalent in its structure to the naturally occurring human FSH in the body.
BRAVELLE ™ (urofollitropin for injection, purified); highly purified human-derived FSH (Hfsh) only human-derived FSH approved for both subcutaneous (SC) and intramuscular (IM) injection.
PRP (prolactin releasing peptide)

hPRP Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-Gly-Arg-Phe-NH2
LIF

Emfilermin (r-LIF) embryo implantation failure: still in clinical studies (NOT YET APPROVED)
EPO NeoRecormon, Erythropoietin beta; Roche
epoetin omega; Baxter International Inc.; physicochemical characteristics different from other erythropoietins or Epos (alpha and beta); currently approved for sale in 15 countries outside of the United States and Western Europe.
darbepoietin
TH Armour Thyroid, natural desiccated thyroid hormone replacement drug, Forest Pharmaceuticals
Cytomel, synthetic liothyronine sodium (T3), King Pharmaceuticals
Levothroid, synthetic levothyroxine, Forest Pharmaceuticals (currently not FDA approved as of Dec. 2003)
Levoxyl, synthetic levothyroxine, from King Pharmaceuticals
Nature-throid and Westhroid, natural desiccated thyroid hormone replacement drug, Western Research Laboratories
Synthroid, synthetic levothyroxine, from Abbott Laboratories
Thyrolar, synthetic liotrix, a combination of L-triiodothyronine (T3) and levothyroxine sodium (T4)
Unithroid, synthetic levothyroxine, from Jerome Stevens Pharmaceuticals
TSH Thyrogen, a synthetic thyroid stimulating hormone (TSH) for use in thyroid cancer patients, from Genzyme Pharmaceuticals, currently FDA approved
TRH (thyroid releasing hormone)

pGlu-His-Pro Amide
THYREL ® TRH (protirelin)

Functional agonists of EPO have been extensively studied. EMP1 (EPO mimetic peptide 1) is one of the EPO mimetics described in Johnson et al., 2000. Short peptide mimetics of EPO are described in, e.g., Wrighton et al., 1996 and U.S. Pat. No. 5,773,569. Small molecular EPO mimetics are disclosed in, e.g., Kaushansky, 2001. Antibodies that activate the EPO receptor are described in, e.g., U.S. Pat. No. 5,885,574; WO 96/40231 and WO 97/48729).

Antibodies that have agonist activities for the EGF receptor are described, e.g., in Fernandez-Pol, 1985 and U.S. Pat. No. 5,723,115. In addition, activating amino acid sequences are also disclosed in U.S. Pat. No. 6,333,031 for the EPO receptor, EGF receptor, prolactin receptor and many other cell surface receptors; metal complexed receptor ligands with agonist activities for the prolactin and EPO receptors can be found in U.S. Pat. No. 6,413,952. Other methods of identify- It should be noted that the effective amount of each analog, variant or functional agonist may be different from that for the native agent or compound, and the effective amount in each case can be determined by a person of ordinary skill in the art according to the disclosure herein. Preferably, the native agents, or analogs and variants that share substantial sequence similarity with the native agents, are used in the present invention.

Pharmaceutical compositions are also provided, comprising an LH/hCG, an additional agent as described above, and a pharmaceutically acceptable excipient and/or carrier.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally.

For example, it is shown in Example 6 that intramuscular injection is an efficient route of delivering hCG to exert its function in the brain. Preferably, the composition is delivered into the central nervous system by injection or infusion. More preferably it is delivered into a ventricle of the brain, particularly the lateral ventricle. Alternatively, the composition is preferably delivered by systemic routes, such as subcutaneous administration. For example, it has been discovered that prolactin, growth hormone, IGF-1, PACAP and EPO can be effectively delivered by subcutaneous administration to modulate the number of neural stem cells in the subventricular zone.

When the composition is not directly delivered into the brain, and molecules in the composition do not readily cross the blood brain barrier, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine—thienylalanine-serine-proline-4-Me-tyrosine.psi.($CH_2NH$)-arginine-COOH). Alternatively, the molecules can be conjugated to the transferrin receptor antibodies as described in U.S. Pat. Nos. 6,329,508; 6,015,555; 5,833,988 or 5,527,527. The molecules can also be delivered as a fusion protein comprising the molecule and a ligand that is reactive with a brain capillary endothelial cell receptor, such as the transferrin receptor (see, e.g., U.S. Pat. No. 5,977,307).

The pharmaceutical compositions can be prepared by mixing the desired therapeutic agents with an appropriate vehicle suitable for the intended route of administration. In making the pharmaceutical compositions of this invention, the therapeutic agents are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial cerebral spinal fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the therapeutic agents after administration to the patient by employing procedures known in the art.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| TUNEL = | Terminal deoxynucleotidyltransferase-mediated dUTP nick end labeling |
| °C. = | degree Celsius |
| hr = | hour |
| min = | minute |
| μM = | micromolar |

-continued

| | |
|---|---|
| mM = | millimolar |
| M = | molar ml milliliter |
| µl = | microliter |
| mg = | milligram |
| µg = | microgram |
| FBS = | fetal bovine serum |
| PBS = | phosphate buffered saline |
| DMEM = | Dulbecco's modified Eagle's medium |
| MEM = | modified Eagle's medium |
| EGF = | epidermal growth factor |
| NSC = | neural stem cell |
| SVZ = | subventricular zone |
| PACAP = | pituitary adenylate cyclase activating polypeptide |
| cAMP = | cyclic AMP |
| BMP = | bone morphogenetic protein |
| CSF = | cerebral spinal fluid |

Materials and Methods

Female Mice Exposed to Male Mice Odor

Mice (CD1, 10 weeks old) were continuously exposed to the odor of the opposite gender or the same gender over a two-week time course. A social interaction component was not part of this study. Instead the mice were only exposed to the odors of the opposite gender. This was necessary to control for confounds that would arise if done otherwise. For example, if males were placed together with females this would give the animals the opportunity to mate. Fowler's study on prairie voles (2002) has shown increased neurogenesis in pregnant female voles, and even more significantly, the study of Shingo et al. (2003) showed that both pregnancy and mating alone could result in an increase in neurogenesis. Therefore, if a neurogenic effect was seen it would be impossible to conclude that it was mediated by odor exposure alone.

With this in mind, a two-week continuous exposure protocol was established to conduct this study, where the duration of the time course was chosen to account for the variable nature of neuronal cell proliferation in different environmental conditions. This also ensured that a surge in neuronal progenitor cell proliferation would not be overlooked because previous behavioral studies have shown increases in neuronal progenitor cells varying from a one-day period to a two-week period (Kempermann and Gage, 1999; Fowler et al., 2002).

Briefly, male mice were placed in a clean cage for two days. The male mice were then removed from the male odorized cage, and female mice were housed in the cage for a desired length of time.

A total of 18 female (CD-1, 10 week old) mice were first chosen to experience a continuous exposure to male (CD-1, 10 week old) or female mice odor. Of the 18, 3 were randomly assigned to be exposed for 2 days to male odor. Another 3 were chosen to participate in the 7-day male odor exposure and another 3 in the 14-day male odor exposure condition. Similarly, an additional 3 were randomly assigned to experience 2 days of female odor. Another 3 were chosen to participate in the 7-day female odor exposure condition and the remaining 3 were placed in the 14-day female odor exposure condition.

Thus, in the first step, 9 male mice were placed into clean cages for 2 days. After the males odorized their cages for two days, they were transferred to a new clean cage. Then the females were transferred to the male odorized cage for 2 days to experience the odor of the opposite gender. For the females assigned to the 2-day exposure the time course was complete; however those assigned to the 7 and 14 day exposures would have to repeat the sequence, essentially being transferred to a fresh odorized cage odorized by the same males to complete their time course.

To compare the effects of whether exposing females to opposite gender odor over the time course may have on neurogenesis, the remaining 9 female mice selected above were to also experience a continuous gender odor, but odor of the same gender, under the same schematic as outlined above.

Upon the termination date of a group's time course, BrdU injections were given to the mice to label proliferating cells in the SVZ. Further immunohistochemical analysis were done and are outlined below.

Immunohistochemistry

To examine the number of progenitor cells in the SVZ after treatment, bromodeoxyuridine (BrdU) injections were used to label these cells. Animals received BrdU injections (120 mg/kg, i.p., dissolved in 0.007% NaOH in phosphate buffer) every 2 hours for a 10 hour period. Each injection of BrdU will only label proliferating cells in the S-phase and the purpose of having a series of BrdU injection is to ensure the continuing availability of BrdU for full incorporation (Morshead and van der Kooy, 1992).

The animals were sacrificed by anaesthetic overdose and perfused transcardially with 4% paraformaldehyde in PBS, pH 7.2. Brains were post-fixed in the same paraformaldehyde solution overnight at 4° C., and cyroprotected for 24 hours in 20% sucrose in PBS. The brains were then embedded in Tissue Tek O.C.T. compound (Sakura Fineteck, Torrance, Calif.) before being cyrosectioned at 14 µm.

The antibodies used for staining were rat anti-BrdU and guinea pig anti-DCX.

The sections were post-fixed with acetone for 30 seconds at room temperature and washed with PBS. For BrdU staining, the tissue was treated with 1M HCl for 22 minutes at 60° C. to denature cellular DNA. Sections were then incubated for 24 hours at room temperature in primary antibody (rat anti-BrdU, 1:50) diluted in 0.3% PBS-T containing 10% NGS, washed with PBS, and then incubated with goat-anti-rat secondary antibodies conjugated to biotin (1:200) for 1 hour at room temperature. After rinsing with ddH$_2$O, sections were mounted with Fluorosave, because staining was visualized with CY3-Streptavodin, and viewed with a Zeiss Axiophot fluorescence microscope.

For DCX staining, sections were incubated for 24 hrs at room temperature in primary antibody (goat anti-DCX, 1:500) diluted in 0.3% PBS-T containing 10% NGS, washed with PBS, and then incubated with donkey anti-goat biotin secondary antibody for 1 hour at room temperature. After rinsing, an amplification procedure was performed by washing the slides with PBS and incubating them with CY3-Streptavodin and Hoechst for 1 hour at room temperature. After rinsing with ddH$_2$0, sections were mounted with Fluorosave and viewed with a Zeiss Axiophot.

Quantification of Immunohistochemistry Results

BrdU in the SVZ: A one-in-ten series of coronal sections (14 µm) from the rostral tip of the lateral ventricle to caudal most aspect of the ventricles (total 10 sections) were collected. BrdU-positive cells were then counted in the defining ependymal-subependymal layer.

DCX in the dorsolateral corner of the SVZ: A one-in ten series of coronal sections (14 µm) from the rostral tip of the lateral ventricle to 980 µm caudal of the ventricles (total 10 sections) was performed. DCX-positive cells were then counted in the dorsolateral corner.

Male Mice Exposed to Female Mice Odor

To see if opposite gender odor had any effect of male mice, the same methodology was used to continuously expose male mice to female mice odor. The identical time course of 2-day, 7-day, and 14-day odor exposure to female mice was used, as well as a 2-day, 7-day, and 14-day odor exposure to male mice for comparison. Immunohistochemical and quantification components were also identical to the design for the females.

Neural Stem Cell Culture and Growth Factors

Generation and differentiation of spheres from embryonic and adult forebrain were performed as described previously with minor modifications (Reynolds and Weiss, 1992; Reynolds et al., 1992). Briefly, striato-pallidum complexes were removed from mouse embryos at E14 and collected into PBS containing 0.6% glucose, penicillin (50 U/ml), and streptomycin (50 U/ml; both from Life Technologies, Gaithersburg, Md.) and then transferred into the standard culture medium composed of DMEM-F-12 (1:1), glucose (0.6%), glutamine (2 mM), sodium bicarbonate (3 mM), HEPES buffer (5 mM), insulin (25 µg/ml), transferrin (100 µg/ml), progesterone (20 nM), putrescine (60 µM), and selenium chloride (30 nM) (all from Sigma, St. Louis, Mo., except glutamine from Life Technologies). For adult neural stem cell cultures, medial and lateral portions of the lateral ventricle subependyma from the adult brain were dissected from both hemispheres, pooled together, subsequently cut into 1 mm$^2$ fragments, and transferred into the standard culture medium containing 1.33 mg/ml trypsin, 0.67 mg/ml hyaluronidase, and 0.2 mg/ml kynurenic acid (all from Sigma). After 30 min at 37° C., the tissue was transferred to the standard culture medium containing 0.7 mg/ml trypsin inhibitor (Roche Diagnostics, Laval, Quebec, Canada). Tissue pieces were mechanically dissociated with micropipettes. Cells were seeded at various densities into the standard culture medium, which also contained EGF (20 ng/ml human recombinant; Peprotech, Rocky Hill, N.J.). Cells were cultured for 7 days in vitro (DIV) and formed floating cell clusters (spheres). All the mice for culture experiments were killed by cervical dislocation.

Implantation of the Osmotic Pumps and Growth Factor Infusion

Sixteen 8-week-old CD-1 mice (Charles-River, Laval, Quebec, Canada) were anesthetized with sodium pentobarbital (120 mg/kg, i.p.) and implanted with osmotic pumps (Alzet 1007D; Alza, Palo Alto, Calif.). The cannulas were located in the right lateral ventricle (anteroposterior +0.2 mm, lateral +0.8 mm to bregma, and dorsoventral 2.5 mm below dura with the skull leveled between lambda and bregma). LH (33 µg/ml human LH derived from the pituitary; the National hormone and peptide program, University of California Los Angeles, Calif., USA) was dissolved in 0.9% saline containing 1 mg/ml mouse serum albumin (Sigma). Each animal was infused for 6 d with either vehicle alone or LH at a flow rate of 0.5 µl/hr, resulting in a delivery of 400 ng/d of LH.

The TUNEL Assay

TUNEL labeling was performed using the ROCHE In Situ Cell Death Kit (cat #1 684 795) according to the manufacturers instructions for use on frozen tissue.

Example 1

Odors of the Opposite Gender Stimulates Proliferation

To determine the impact of male or female odors, adult mice were exposed to the odors of the opposite gender for 2 days, 7 days or 14 days. A control group was exposed to the odors of the same gender for the same period of time. The mice then received BrdU to label proliferating cells, and the locations of the BrdU positive cells were identified by immunohistochemical studies. Female or male mice were also exposed to control unodorized cages in parallel experiments for 7 days (female) or 2 days (male), and these animals did not differ from animals exposed to same sex odors (data not shown)

As shown in FIG. 1A, proliferating cells in the SVZ of female mice remained at the same level after being exposed to female odors for 2, 7 or 14 days. In the female group exposed to male odors, however, proliferating cells in the SVZ changed with time: increased significantly after 7 days and decreased significantly after 14 days. A 2-day exposure had no significant effect. The same pattern was observed when Ki67 was used to label proliferating cells (FIG. 1B), indicating that the change in BrdU positive cells reflected a change of proliferation level rather than preferred uptake of BrdU.

Figure 1C:
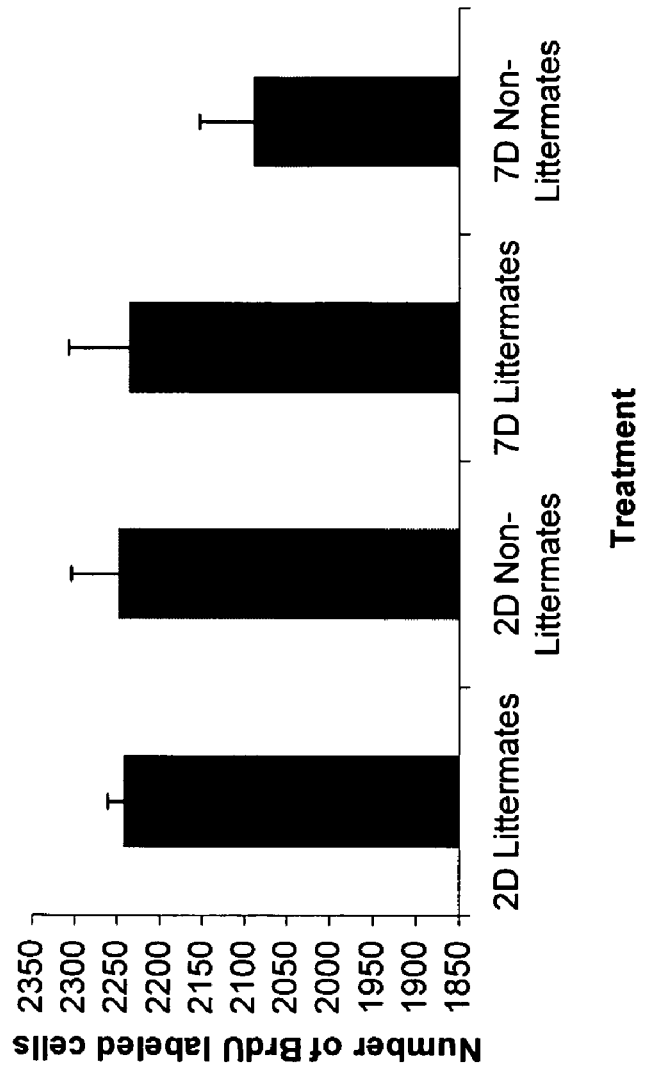

The male and female mice used in the above experiments were from the same litter or previously shipped together. Therefore, they had been exposed to the odor of one another before the experiments were performed. To rule out the possibility that this effect was specific to littermates or animals that have been pre-exposed to the odor of interest, mice from different litters that had not previously been in the same place were used to repeat the experiments. Similar effects were observed whether the mice were littermates or not (FIG. 1C), indicating that the effects of the male odor are not limited to particular litters or pre-exposure of the odor.

Figure 2C:
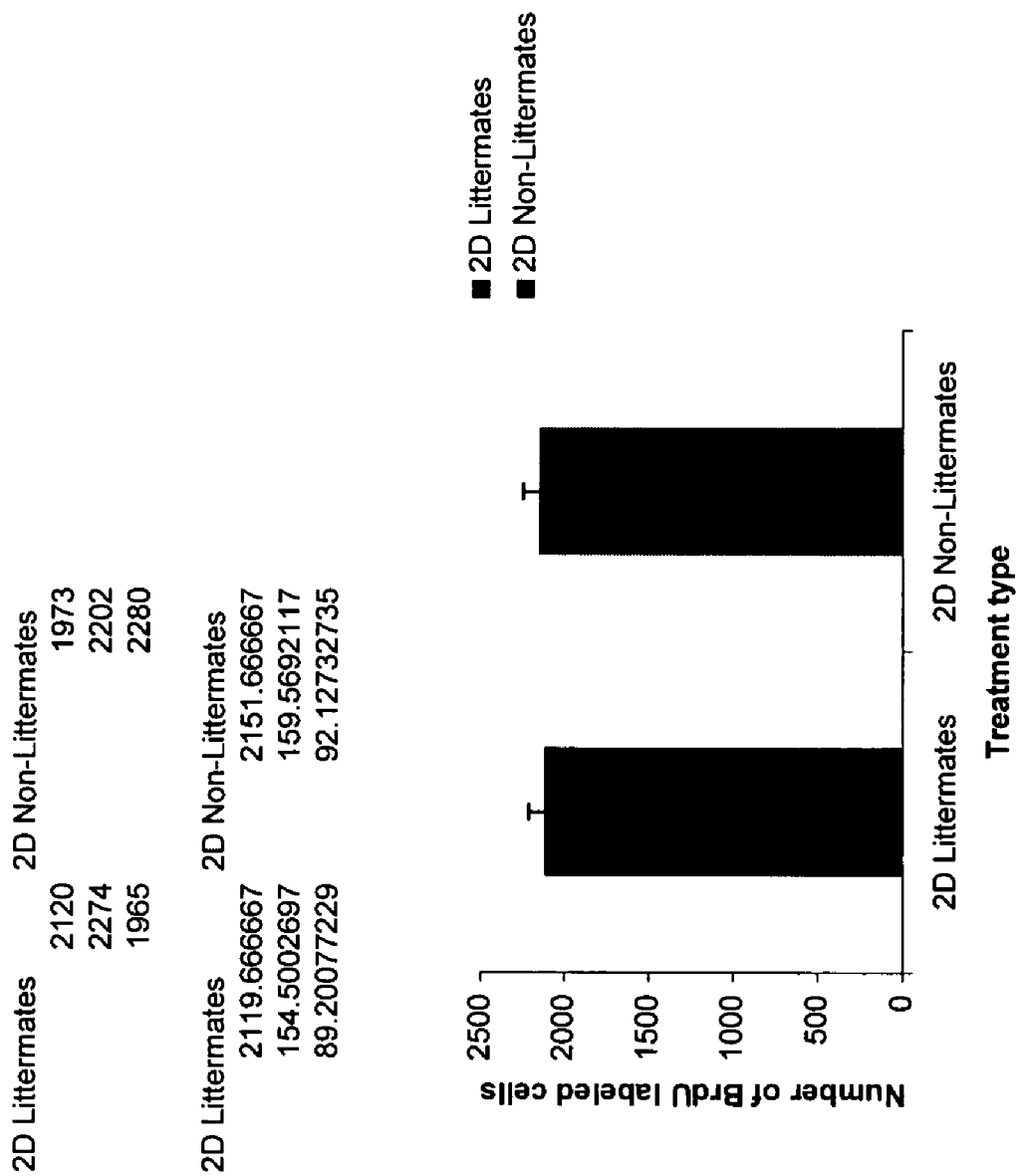

Female odors also affected proliferation in male mouse brains, but in a different temporal pattern. When males were exposed to female odors for 2 days, there was a sudden increase in the number of BrdU positive cells (FIG. 2A) or Ki67 positive cells (FIG. 2B). After a 7 or 14 day exposure, however, the number of newly proliferated cells decreased to the control level. As with the female mice, the effects of female odors could be observed when different litters were used (FIG. 2C).

Striking, the neural stem cells in the hippocampus also responded to gender-specific odors. Again, exposure for two days to male odors had no significant effects on female mice, but a 7-day exposure resulted in a significant increase in proliferation in the hippocampus (FIG. 3). After an exposure for 14 days, levels of proliferating cells were significantly lower in females exposed to male odors when compared with the females that had been exposed to female odors. To our knowledge, this is the first time that any stimulus, other than growth factors (e.g., EGF plus FGF), is shown to exert the same effects on the neural stem cells in the SVZ and the hippocampus.

As an additional control, female mice were exposed to odors of castrated male mice for 7 days. The results show that the numbers of BrdU labeled cells in either the SVZ or hippocampus did not increase in these females, as compared to females that had been exposed to sham male odors. Sham male odors are odorized cages that were odorized by male mice that underwent a sham castration surgery. Females exposed to the odors of these sham castrated males showed sex pheromone-induced neurogenesis, however females exposed to the odors of castrated males did not show increased neurogenesis. Similarly, male mice exposed to the odors of adrenalectomized females for two days also showed no increase in the number of BrdU labeled cells in the SVZ or the hippocampus, as compared to males exposed to sham female odors. Castration and adrenalectomy are known to reduce pheromone levels (Ma et al., 1998; Kiyokawa et al., 2004; Zhang J. et al. (2001)). These results thus further support the observation that pheromones induce neural stem cell proliferation in both the SVZ and hippocampus of the opposite gender.

Example 2

Odors of the Opposite Gender Stimulates Neurogenesis but not Cell Survival

Neurogenesis was also enhanced upon exposure to the odors of the opposite gender. Thus, tissue sections from Example 1 were stained for doublecortin, a cytoplasmic protein expressed in neuronal progenitor cells, to determine the extent of neurogenesis in the mice described above. As in the case of proliferating cells, female mice had significantly more doublecortin positive cells after a 7-day exposure to male odors (FIG. 4) while male mice had significantly more doublecortin positive cells after a 2-day exposure to female odors (FIG. 5).

To determine if pheromones from the opposite gender also impact survival of neural cells, the TUNEL assay was performed. The results indicate that no significant difference can be observed in the SVZ (FIG. 6A) or olfactory bulb (FIG. 6B) of female mice after a 7-day exposure to male odors.

Example 3

The Effects of LH In Vivo and In Vitro

Male pheromones are known to increase the levels of the luteinizing hormone (LH) and decrease the levels of prolactin, while female pheromones are associated with an increase of prolactin (Dulac et al., 2003). In an attempt to investigate how pheromones enhance neural stem cell proliferation and neurogenesis in the opposite gender, animals were infused with LH as described in Materials and Methods. Indeed, LH increase proliferation significantly in the SVZ of both female (FIGS. 7A and 7B) and male mice (FIG. 8).

To confirm that LH stimulates proliferation of neural stem cells, neural stem cell cultures were established as described in Materials and Methods. Primary spheres were dissociated and plated in the presence of EGF or EGF plus LH (30 nM) at limited density to allow formation of secondary spheres. The number of secondary spheres were counted, and the results are shown below:

Neural stem cells isolated from female mice:

|         | EGF   | EGF + LH |
|---------|-------|----------|
| Exp. #1 | 172.3 | 255.9    |
| Exp. #2 | 157.6 | 241.9    |
| Exp. #3 | 197.9 | 258.9    |

Neural stem cells isolated from male mice:

|         | EGF   | EGF + LH |
|---------|-------|----------|
| Exp. #1 | 144.4 | 168.6    |
| Exp. #2 | 225.1 | 275.1    |
| Exp. #3 | 168.2 | 195.9    |

Thus, LH is also capable of increasing self-renewal of neural stem cells in culture, and it is more effective on the neural stem cells isolated from female mice than those isolated from male mice.

Example 4

The Effects of hCG In Vivo and In Vitro

HCG has the same activity as LH. When mice are infused with a recombinant hCG (choriogonadotropin alfa; Ovidrel®/Ovitrelle®1) or vehicle alone according to the protocol described in Materials and Methods, it is discovered that hCG significantly increases proliferation in the SVZ in both male and female mice. Proliferating cells in the hippocampus also increase significantly in both gender.

Neurogenesis is also assessed by using a neuron marker, doublecortin or NeuN. The number of doublecortin or NeuN positive cells in the SVZ or olfactory bulb is significantly higher in the mice infused with hCG.

To confirm that hCG stimulates proliferation of neural stem cells, neural stem cell cultures are established as described in Materials and Methods. Primary spheres are dissociated and plated in the presence of EGF or EGF plus choriogonadotropin alfa at limited density to allow formation of secondary spheres. The number of secondary spheres are then counted, and the results indicate that hCG significantly increases the number of secondary spheres whether the neural stem cells are from male or female animals.

Example 5

The Effects of Additional Agents

An additional agent, prolactin, is included in the experiments described in Example 3 or 4. Thus, mice are infused with:
(1) a combination of LH and prolactin or hCG and prolactin;
(2) LH or hCG; or
(3) vehicle alone (control).

The results show that while LH or hCG increases proliferation in the SVZ as compared to the control group, the addition of prolactin further enhances the effects of LH or hCG. Similarly, when prolactin is added with LH or hCG in neural stem cell cultures, self-renewal (the number of secondary spheres from primary spheres) is enhanced.

Similarly, Epo (NeoRecormon) is included with LH or hCG to determine its effects on neurogenesis, and the results show that Epo enhanced the number of doublecortin positive cells over the level achieved by LH or hCG alone.

Although the Examples described above employ specific agents, it should be noted that any analog or variant of LH/hCG, including the compounds listed in Table 1, can be used as LH or hCG. Similarly, any additional agent capable of enhancing neurogenesis and analog/variant thereof, including those listed in Table 2, can be used in Example 5 in the place of NeoRecormon. Glial cell formation can be practiced using the methods described herein and knowledge available in the art.

Example 6

Intramuscular Delivery of hCG

Human chorionic gonadotropin (hCG) and luteinizing hormone (LH) are commercially available drugs for human use, marketed as Pregnyl and Profasi, respectively. The maximal safe dose for each of these drugs is 10,000 USP units per day via intramuscular injection. This corresponds to approximately a 5.0 USP unit dose for a mouse of 30 grams. To test whether this dose would be sufficient to induce forebrain neurogenesis in mice, we performed the following experiment.

Six to eight week old female CD-1 mice received a single intramuscular injection of 5.0 USP units of recombinant hCG (Sigma Catalog Number C 6322) in a 0.05 ml volume (diluted in saline). Control mice received a single injection of saline alone. The mice then received 6 injections of BrdU (120 mg/kg), one every two hours, beginning two hours after the hCG injection. The mice were sacrificed thirty-minutes after the last BrdU injection, perfused transcardially with 4% paraformaldehyde, and the tissue was processed for cryosectioning. Brains were sectioned serially at 14 microns onto two sets of seven slides each, 12 sections on each slide. The number of BrdU positive cells was counted in the forebrain SVZ on one slide for each of the control and hCG injected animals. The following data are the average numbers of BrdU+ cells per section in the control (saline only) and hCG-injected mice, respectively.

Saline: 163±6 (n=4)

hCG: 206±13 (n=4; *p<0.02; paired t-test)

Therefore, a single low dose hCG injection increased proliferation in the forebrain SVZ by 26%.

Example 7

LH Receptor Knock-Out Mice Experiments

To investigate whether the LH receptor directly mediates the effects of LH on the neural stem cells in the SVZ and hippocampus, we determined the levels of LH receptors in both areas using immunohistochemical analyses. The results indicate that LH receptors can be found in both SVZ and hippocampus in male and female mice, although the males had lower levels of LH receptors compared to the females. Thus, LH probably binds directly to its receptors in the SVZ and hippocampus to trigger the biological functions described herein.

To further investigate the role of LH, LH receptor (LHR) knock-out (KO) mice were used in the odor-exposure experiments as described in Example 1. The mice were previously described in Zhang, F. P. et al., 2001, and Huhtaniemi et al., 2002. Eight to ten week old adult LHR wildtype (WT) and KO mice were exposed to the odors of the opposite gender for 2 or 7 days. On the 2nd (male exposed to female odor) and 7th day (female exposed to male odor) of exposure the animals received 6 injections of BrdU (120 mg/kg), once every two hours. The mice were then sacrificed and transcardially perfused with 4% paraformaldehyde, about 30 minutes following the last injection, and the tissue was processed for cryosectioning. The forebrains of the mice were serially cryosectioned at 14 microns onto 7 slides, with 10 sections on each slide. A single slide from each animal was then immunostained for BrdU, and the total number of BrdU positive cells in the SVZ was quantified. Mice that were exposed to unodorized cages are used as baseline controls.

The results are shown in FIGS. 9 and 10. As expected, male odor resulted in an increase of proliferation in both the SVZ and hippocampus of female wild type mice (+/+) (FIGS. 9A and 9B). In the LHR knock-out mice (−/−), however, no increase of proliferation was observed in the hippocampus after exposure to male odor (FIG. 9B). These results indicate that LH receptor signaling is important for the effects of male pheromones in the hippocampus of female mice. Interestingly, the lack of LH receptor did not affect proliferation in the SVZ in response to male pheromones (FIG. 9A). Similarly, in male mice, LH receptor knock-out had no impact on female pheromone-induced proliferation in either the SVZ or hippocampus (FIG. 10). Thus, although LH is sufficient to induce neural stem cell proliferation in the SVZ and hippocampus in both females and males, there is a factor (or factors) that can also mediate the actions of pheromones in the SVZ and the male hippocampus.

We claim:

1. A method of enhancing neurogenesis in a mammal in need thereof, comprising administering an effective amount of a luteinizing hormone (LH) and erythropoietin (EPO) or a human chorionic gonadotropin (hCG) and EPO to the mammal, wherein neurogenesis is enhanced in the mammal.

2. The method of claim 1 wherein the mammal is an adult.

3. The method of claim 1 wherein the neurogenesis occurs in the subventricular zone.

4. The method of claim 1 wherein the neurogenesis occurs in the hippocampus.

5. The method of claim 1 wherein the LH or hCG is administered systemically.

6. The method of claim 1 wherein the LH or hCG is administered to the brain of the mammal.

7. The method of claim 1 wherein the mammal has a neurodegenerative disease or condition.

8. The method of claim 7, wherein the neurodegenerative disease is a CNS injury.

9. The method of claim 7, wherein the neurodegenerative disease is a stroke.

10. The method of claim 1, wherein neurogenesis is indicated by the presence of doublecortin-positive or NeuN-positive cells.

11. A method of increasing neural stem cell proliferation in vitro, comprising contacting at least one neural stem cell with an effective amount of a luteinizing hormone (LH) and erythropoietin (EPO) or a human chorionic gonadotropin (hCG) and EPO.

12. The method of claim 11 wherein the neural stem cell is derived from an adult mammal.

13. The method of claim 11 wherein the neural stem cell is derived from the subventricular zone of a mammal.

14. The method of claim 11 wherein the neural stem cell is derived from the hippocampus of a mammal.

15. A method of enhancing neurogenesis in vitro, comprising contacting at least one neural stem cell with an effective amount of a luteinizing hormone (LH) and erythropoietin (EPO) or a human chorionic gonadotropin (hCG) and EPO.

16. The method of claim 15 wherein the neural stem cell is derived from an adult mammal.

17. The method of claim 15 wherein the neural stem cell is derived from the subventricular zone of a mammal.

18. The method of claim 15 wherein the neural stem cell is derived from the hippocampus of a mammal.

* * * * *